(12) United States Patent
Lehn et al.

(10) Patent No.: US 8,124,578 B2
(45) Date of Patent: Feb. 28, 2012

(54) USE OF DYNAMIC MIXTURES FOR A CONTROLLED RELEASE OF FRAGRANCES

(75) Inventors: Jean-Marie Lehn, Strasbourg (FR); Andreas Herrmann, Veyrier (CH)

(73) Assignees: Firmenich SA, Geneva (CH); Universite Louis Pasteur, Strasbourg (FR); Centre National de la Recherche Scientifique, Paris Cedex (FR)

( * ) Notice: Subject to any disclaimer, the term of this patent is extended or adjusted under 35 U.S.C. 154(b) by 814 days.

(21) Appl. No.: 11/669,560

(22) Filed: Jan. 31, 2007

(65) Prior Publication Data
US 2007/0141011 A1  Jun. 21, 2007

Related U.S. Application Data

(63) Continuation of application No. PCT/IB2005/002325, filed on Aug. 3, 2005.

(30) Foreign Application Priority Data

Aug. 5, 2004 (EP) .................................. 04 018 569

(51) Int. Cl.
*A61K 8/18* (2006.01)
*A61Q 13/00* (2006.01)

(52) U.S. Cl. ......................................................... 512/27
(58) Field of Classification Search ..................... 512/27
See application file for complete search history.

(56) References Cited

U.S. PATENT DOCUMENTS

| 4,209,025 | A | * | 6/1980 | Wilson et al. | 131/279 |
|---|---|---|---|---|---|
| 4,279,891 | A | * | 7/1981 | Henkel et al. | 424/73 |
| 4,331,611 | A | * | 5/1982 | Mookherjee et al. | 558/432 |
| 4,708,821 | A | | 11/1987 | Shimokawa et al. | 512/12 |
| 5,919,752 | A | * | 7/1999 | Morelli et al. | 512/1 |
| 6,413,920 | B1 | * | 7/2002 | Bettiol et al. | 510/101 |
| 7,795,465 | B2 | * | 9/2010 | Zierke et al. | 558/417 |
| 2001/0014661 | A1 | | 8/2001 | Herrmann | 512/27 |
| 2004/0028745 | A1 | * | 2/2004 | Bouhadir et al. | 424/488 |
| 2004/0029172 | A1 | | 2/2004 | Lehn et al. | 435/7.1 |
| 2004/0220064 | A1 | * | 11/2004 | McGee et al. | 510/130 |

FOREIGN PATENT DOCUMENTS
EP  1 184 359 A1  3/2002
WO  WO 2005090293 A1 * 9/2005

OTHER PUBLICATIONS

MSDS sheet taken from ScienceLab.com updated on Oct. 9, 2005.*
MSDS sheet taken from http://msds.chem.ox.ac.uk/CI/cinnamaldehyde.html updated on Aug. 25, 2004.*

(Continued)

*Primary Examiner* — Benjamin Packard
(74) *Attorney, Agent, or Firm* — Winston & Strawn LLP

(57) ABSTRACT

The present invention relates to a delivery system in the form of a dynamic mixture obtained by reacting together, in the presence of water, at least one hydrazine derivative with at least one perfuming, flavoring, insect repellent or attractant, bactericide or fungicide aldehyde or ketone. The inventive mixture is capable of releasing in a controlled and prolonged manner the aldehyde or ketone in the surrounding environment. Furthermore, the present invention concerns also the use of these dynamic mixtures as perfuming ingredients as well as the perfuming compositions or perfumed articles that include such mixtures.

17 Claims, 2 Drawing Sheets

UV/Vis spectra obtained for the formation of the dynamic mixture by admixing a hydrazine derivative (I) and an active aldehyde (top) and by hydrolysis of the corresponding hydrazone derivative 1c (bottom) at pH 2.47.

OTHER PUBLICATIONS

MBI benzaldehyde MSDS sheet, Nov. 17, 1999.*
Controlled release of volatile aldehydes and ketones by reversible hydrazone formation—"classical" profragrances are getting dynamic Barbara Levrand, et al Received (in Cambridge, UK) Feb. 15, 2006, Accepted Mar. 20, 2006 First published as an Advance Article on the web Apr. 3, 2006.*
MSDS shhet taken from http://msds.chem.ox.ac.uk/CI/cinnamaldehyde.html updated 25, 2004.*

* cited by examiner

Figure (I): UV/Vis spectra obtained for the formation of the dynamic mixture by admixing a hydrazine derivative (I) and an active aldehyde (top) and by hydrolysis of the corresponding hydrazone derivative 1c (bottom) at pH 2.47.
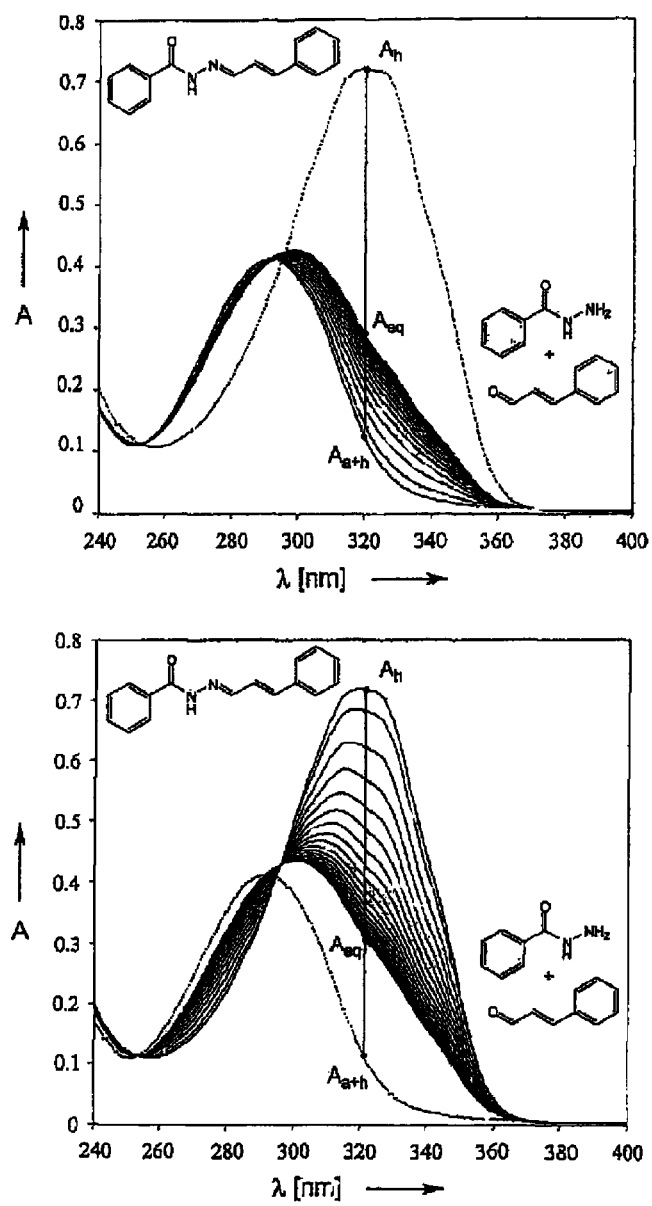

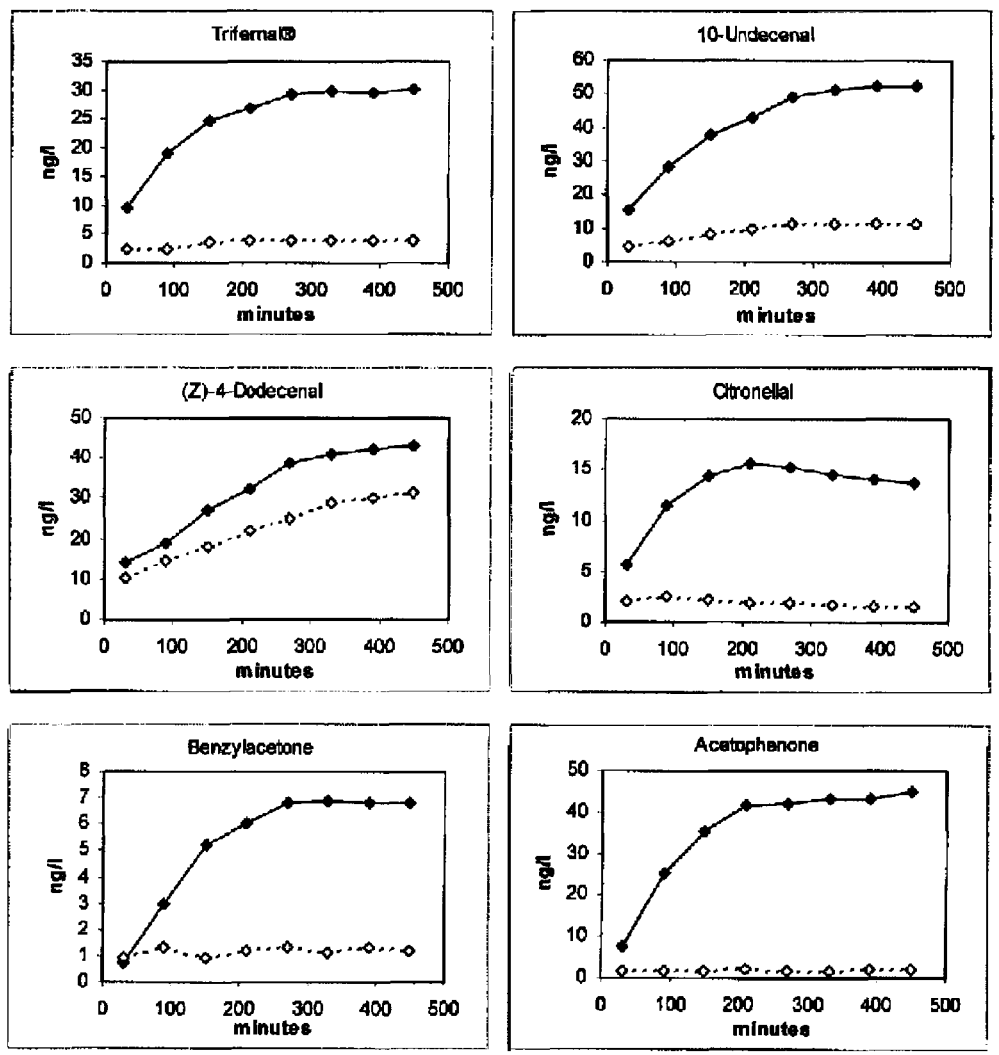
Figure (II): Comparison of the concentration in the headspace of perfumery aldehydes and ketones in the presence and absence of hydrazine derivative 3a on dry fabric as obtained by dynamic headspace analysis (presence of 3a —— solid line; absence of 3a ---- dashed line):

US 8,124,578 B2

USE OF DYNAMIC MIXTURES FOR A CONTROLLED RELEASE OF FRAGRANCES

CROSS-REFERENCE TO RELATED APPLICATIONS

This application is a continuation of International application PCT/IB2005/002325 filed on Aug. 3, 2005, the entire content of which is expressly incorporated herein by reference thereto.

TECHNICAL FIELD

The present invention concerns a dynamic mixture obtained by combining, in the presence of water, at least one hydrazine derivative with at least one active aldehyde or ketone. The invention's mixture is capable of releasing in a controlled and prolonged manner the active compound in the surrounding environment.

BACKGROUND

Active compounds, such as fragrances, but also insect attractants or repellents, as well as some bactericides, are volatile molecules that can only be perceived over a limited period of time. For instance, the perfume industry has a particular interest for compositions or additives which are capable of prolonging or enhancing the perfuming effect of fragrances over a certain period of time, for example in order to overcome the problems encountered when using perfuming ingredients as such, which are too volatile or have a poor substantivity or are only deposited in a small amount onto the surface of the final application. These compositions or additives can be used in various applications, as for example in fine or functional perfumery or in cosmetic preparations. The washing of textiles is a particular field in which there is a constant quest to enable the effect of active substances, in particular perfumes, to be effective for a certain period of time after washing and drying. Indeed, many substances having odors which are particularly suitable for this type of application are known to lack tenacity on laundry, or do not remain on the laundry when rinsed, with the result that their perfuming effect is experienced only briefly and not very intensely. Given the importance of this type of application in the perfume industry, research in this field has been sustained, in particular with the aim of finding new, and more effective solutions to the aforementioned problems.

A variety of chemical delivery systems which release active material by a chemical reaction during or after application (using $O_2$, light, enzymes, water (pH) or temperature as the release trigger) have been described as an alternative to encapsulation systems. In general, due to their inherent instability, the precursors often decompose in the application base during storage and thus release their fragrance raw material before the desired use.

To the best of our knowledge, none of the compositions of the present invention are known from the prior art and no hydrazine derivatives have been described for a use as disclosed further below.

Dynamic libraries using hydrazines and carbonyl derivatives are known from the pharmaceutical industry. However, in such prior art libraries, the ketones or aldehydes are pharmaceutically active compounds, and the libraries themselves are either used to generate a multitude of more or less biologically active compounds or for rapid identifications of biological receptors or ligands. None of the prior art documents suggest, or allow to reasonably expect, that the reversibility of the formation of addition products between carbonyl compounds and hydrazine derivatives may allow to deliver the carbonyl compounds in a controlled manner or that such libraries can be used successfully as perfuming ingredients or even that they allow to prolong the fragrancing effect of a perfuming compound, especially in a consumer product.

SUMMARY OF THE INVENTION

The present invention now relates about dynamic mixtures for the controlled release of active ingredients. These dynamic mixtures can be obtained by combining, in the presence of water, at least one hydrazine derivative with at least one active aldehydes/ketones. The use of the inventive mixture allows to achieve a controlled and prolonged release of active aldehydes/ketones in the surrounding environment.

Furthermore, the present invention concerns also the use of the dynamic mixtures as perfuming ingredients as well as the perfuming compositions or perfumed articles comprising the invention's mixtures. A further object of the present invention is the use of specific hydrazine derivatives as additives to prolong the perfuming effect of particular aldehydes or ketones.

BRIEF DESCRIPTION OF THE DRAWINGS

The experimental spectra obtained for the reversible reaction and the comparison graphs are presented in the drawings and description that follows, wherein:

Figure I (top) is the UV/Vis spectra obtained for the formation of the dynamic mixture by admixing a hydrazine derivative and an active aldehyde.

Figure I (bottom) is the UV/Vis spectra obtained for the hydrolysis of the corresponding hydrazone derivative 1c at pH 2.47.

Figure II is a comparison of the concentrations in the headspace of the perfumery aldehydes and ketones in the presence and absence of hydrazine derivative 3a.

DETAILED DESCRIPTION OF THE PREFERRED EMBODIMENTS

We have now surprisingly found that a dynamic mixture, obtainable by combining, in the presence of water, at least one hydrazine derivative with at least one active aldehyde or ketone is a valuable ingredient capable of releasing, in a controlled and prolonged manner, the active aldehyde or ketone as shown in Fig. II.

As "dynamic mixture" we mean here a composition comprising a solvent, several starting components as well as several addition products that are the results of reversible reactions between the various starting components. The dynamic mixtures take advantage from reversible chemical reactions, in particular hydrazone formation and dissociation by reversible hydrazine/carbonyl condensation. The change in the UV/Vis spectra upon admixing the hydrazine derivative and active aldehyde, and the change upon hydrolysis of the hydrazone derivative is shown in Fig. I, indicating the reversibility of the reaction. The ratio between the various starting and addition products depends on the equilibrium constant of each possible reaction between the starting components. The usefulness of the "dynamic mixture" derives by a synergistic effect between all the components.

As the term "active" we mean here that the aldehyde or ketone to which it is referred is capable of bringing a benefit or effect into its surrounding environment, and in particular a perfuming, flavoring, insect repellent or attractant, bactericide and/or fungicide effect. Therefore, for example, the "active aldehyde or ketone" possesses at least one property which renders it useful as perfuming or flavoring ingredient, as insect repellent or attractant or as bactericide or fungicide.

According to all the above and below mentioned embodiments of the invention, the invention's delivery system is particularly useful when the active aldehyde or ketone is a perfuming ingredient, i.e. a perfuming aldehyde or ketone. A "perfuming aldehyde or ketone" is a compound, which is of current use in the perfumery industry, i.e. a compound which is used as active ingredient in perfuming preparations or compositions in order to impart a hedonic effect. In other words, such an aldehyde or ketone, to be considered as being a perfuming one, must be recognized by a person skilled in the art of perfumery as being able to impart or modify in a positive or pleasant way the odor of a composition, and not just as having an odor. From now on we will refer to the "perfuming aldehyde or ketone" also as "perfuming compounds".

In general, the invention is carried out exactly in the same manner, independently of the exact properties of the active aldehyde or ketone. Therefore, it is understood that, even if the invention will be further illustrated hereinbelow with a specific reference to "perfuming compounds", the below embodiments are also applicable to other active aldehydes or ketones (i.e. it is possible to replace the expression "perfuming" with "insect attractant" or with "insect repellent and bactericide", for instance).

Now, according to a particular embodiment of the invention, the present invention concerns a delivery system in the form of a dynamic mixture, obtainable by reacting, in a water-containing medium, i) at least one hydrazine derivative of formula

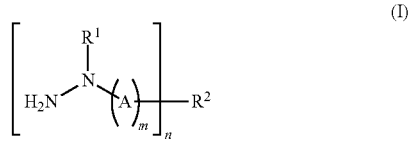

(I)

wherein a) $R^1$ represents a hydrogen atom, a $C_1$ to $C_5$ alkyl group or a phenyl group optionally substituted by up to three $R^3$ groups;
$R^3$ representing a group selected from the group consisting of OR, $NR_2$, $SO_3R$, $C_{1-4}$ alkyl group and COOR, R representing a hydrogen atom, a $C_1$ to $C_{10}$ alkyl or polyethylene- or polypropylene-glycol group, a phenyl group or a $C_6$ to $C_9$ alkylaryl group;
A represents a functional group selected from the group consisting of C=O, $SO_2$, C=S and C=NR; and
I) m is 0 or 1; n is 1, 2, 3 or 4; and $R^2$ represents a mono-, di-, tri- or tetra-radical derived from a $C_1$ to $C_{18}$ linear, branched or cyclic hydrocarbon group, preferably alkyl, optionally comprising one, two, or three nitrogen or oxygen atoms, or derived from a phenyl group, or derived from a $C_{4-5}$ hetero-aromatic group, the $R^2$ being optionally substituted by up to three $R^3$ groups; or
II) m is 1; n is 1, 2 or 3; and $R^2$ represents a $N(R^4)_{3-n}$ group, $R^4$ representing a $R^1$ group or a $R^3CO$ group; or
III) m is 1 or 2; n is 1; and $R^2$ represents a $NR^1NH_2$ group;

IV) m is 1; n is 1; and $R^2$ is a $C_1$ to $C_6$ linear, branched or cyclic hydrocarbon, preferably alkyl, group substituted by a $NR_3X$ or a $(NC_5H_4)X$ group ($NC_5H_4$ being a pyridyl group), X representing a halogen atom or a sulphate; or V) m is 0 or 1; n is an integer varying from 2 to 5000; and $R^2$ represents a polyalkylene, polyethyleneglycol, polypropyleneglycol or a polysaccharide chain comprising between 2 and 5000 monomeric units; or b) $R^1$, A and $R^2$, taken together, represent a 5 or 6 membered ring optionally containing up to 4 oxygen, nitrogen or sulphur atoms;

with ii) at least one active aldehyde or ketone having a molecular weight comprised between 80 and 230 g/mol and being a perfuming, flavoring, insect repellent or attractant, bactericide or fungicide ingredient, in particular being selected from the group consisting of the $C_{6-20}$ perfuming aldehydes and the $C_{6-20}$ perfuming ketones.

The dynamic mixture is obtained by reacting one or more hydrazine derivatives with one or more perfuming ingredients in a water-containing medium. By "water-containing medium" we mean here a dispersing medium comprising at least 10% w/w, or even 30% w/w, of water and optionally an aliphatic alcohol such as a $C_1$ to $C_3$ alcohol, for example ethanol. More preferably, the medium comprises at least 50% w/w, or even 70%, water optionally containing up to 30% of a surfactant. According to a particular embodiment of the invention, the water-containing medium may have a pH comprised between 2 and 6.

According to another particular embodiment of the invention, the preferred hydrazine derivatives are those of formula (I) wherein:

$R^1$ represents a hydrogen atom, a methyl or ethyl group, or a phenyl group optionally substituted by one or two $R^3$ groups;

$R^3$ representing a group selected from the group consisting of OR, $NR_2$, $SO_3R$, $C_{1-4}$ alkyl group and COOR, R representing a hydrogen atom, a $C_1$ to $C_5$ alkyl or polyethylene- or polypropylene-glycol group, a phenyl group or a $C_{6-7}$ alkylaryl group;

A represents a functional group selected from the group consisting of C=O, C=S, and $SO_2$; and I) m is 0 or 1; n is 1, 2, 3 or 4; and $R_2$ represents a mono-, di-, tri- or tetra-radical derived from a $C_1$ to $C_6$ linear, branched or cyclic alkyl group, optionally comprising up to three nitrogen or oxygen atoms, or derived from a phenyl group or derived from a $C_{4-5}$ hetero-aromatic group, the $R^2$ being optionally substituted by up to three $R^3$ groups, $R^3$ having the same meaning as above; or II) m is 1; n is 1 or 2; and $R^2$ represents a $N(R^4)_{3-n}$ group, $R^4$ representing a $R^1$ group or a $R^3CO$ group; or III) m is 1 or 2; n is 1; and $R^2$ represents a $NR^1NH_2$ group;

IV) m is 1; n is 1; and $R^2$ is a $C_{1-3}$ linear, branched or cyclic alkyl group substituted by a $NR_3X$ or a $(NC_5H_4)X$ group, X representing a halogen atom; or V) m is 0 or 1; n is an integer varying from 2 to 5000; and $R^2$ represents a polyalkylene, polyethyleneglycol, polypropyleneglycol or a polysaccharide chain comprising between 2 and 5000 monomeric units.

Alternatively, according to a further invention embodiment the hydrazine derivative is a compound of formula

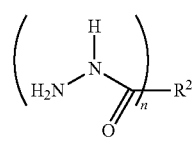

(II)

wherein
I) n is 1, 2, 3 or 4 and $R^2$ represents a mono-, di-, tri- or tetra-radical derived from a $C_1$ to $C_6$ linear, branched or cyclic hydrocarbon group, preferably alkyl, optionally comprising up to two nitrogen or oxygen atoms, or from a phenyl group or from a $C_{4-5}$ hetero-aromatic group, the $R^2$ being optionally substituted by one or two $R^3$ groups;
$R^3$ representing a group selected from the group consisting of OR, $NR_2$, $SO_3R$, $C_{1-4}$ alkyl group and COOR, R representing a hydrogen atom, a $C_1$ to $C_5$ alkyl or polyethylene- or polypropylene-glycol group, a phenyl group or a $C_{6-7}$ alkylaryl group; or
II) n is 1, 2 or 3 and $R^2$ represents a $N(R^4)_{3-n}$ group, $R^4$ representing a hydrogen atom, a methyl or ethyl group or a $R^3CO$ group; or
V) n is an integer varying from 2 to 3000, and $R^2$ represents a polyalkylene, polyethyleneglycol or a polypropyleneglycol chain having a molecular weight comprised between 48 and 80000 or a polysaccharide chain comprising between 2 and 1000 monomeric units derived from galacturonic acid.
Alternatively in the formula (II) $R^2$ is a cationic group, i.e. n is 1 and $R^2$ represents a $CH_2NMe_3X$ or a $CH_2$—$(NC_5H_4)X$ group, X representing a halogen such as chlorine.
In all the above embodiments of the invention, by "polyalkylene chain" we mean here a chain which is derived by the polymerisation of a monomer or co-monomer comprising the moiety of formula —R'C=C(R')$_2$, each R' representing a hydrogen atom or a $C_{1-7}$ group chain such as a $C_{1-3}$ alkyl or even a phenyl group.
More specifically, as non-limiting examples of hydrazine derivatives in the above mentioned embodiments, one may cite the classes:
i) $ArCONHNH_2$ or $ArNHNH_2$, wherein Ar is a substituted or non-substituted $C_{6-9}$ phenyl group, such as phenyl or tolyl or $C_6H_4COOH$, or a $C_{3-5}$ aromatic heterocycle such as furane;
ii) the Girard-T or —P reagents (see A. Girard et al in Helv. Chim. Acta 1936, 19, 1095);
iii) semicarbazones Ar—NH—CO—NHNH$_2$, thiosemicarbazones Ar—NH—CS—NHNH$_2$ or arenesulfonylhydrazines Ar—SO$_2$—NHNH$_2$, wherein Ar is as defined above;
iv) $R^5OCONHNH_2$, wherein $R^5$ is a $C_1$-$C_4$ alkyl group;
v) 4H-1,2,4-triazol-4-amine derivatives;
vi) $(NH_2NHCO)_n$-Alk, wherein n is comprised between 1 and 4 and Alk is a $C_2$-$C_{18}$ linear, branched or cyclic hydrocarbon, preferably alkyl, group optionally substituted by two OH groups and optionally containing one or two nitrogen atoms, such as $C_1$, $C_2$, $C_3$, $C_4$, $C_5$, $C_6$, $C_8$, $C_{12}$, $C_{16}$, $C_{18}$, $(CHOH)_2$, $CH_2(CHOH)_2CH_2$;
vii) $(NH_2NHCOCH_2)_n(R^6)_{2-n}NCH_2CH_2N(R^6)_{2-n}(CH_2CONHNH_2)_n$ or $(NH_2NHCOCH_2)_m(R^6)_{3-m}N$, wherein n is 1 or 2, m is 1, 2 or 3 and $R^6$ is a hydrogen atom or a $R^5$ group;
viii) $Q((CH_2)_dCOOR^6)_{3-n}((CH_2)_dCONHNH_2)_n$, wherein $R^6$ is as defined above, n is 1, 2 or 3 and Q is N or $COR^6$, d being 0 or 1; or
ix) $H_2NNR^6CONR^6NH_2$ or $H_2NNR^6COCONR^6NH_2$, wherein $R^6$ is as defined above;

x) a polyhydrazine derivative of pectin; or
xi) a polyhydrazine derivative of poly(methyl methacrylate) and co-polymers thereof, of poly(methyl acrylate) and co-polymers thereof or of poly(4-vinylbenzoates) and co-polymers thereof.

It is also important to mention that, as a person skilled in the art can foresee, some of the hydrazine derivatives of formula (I), for example those mentioned under iv), can form lipid assemblies such as micelles or liposomes.

The active compounds, and in particular the perfuming ones, are another important element of the dynamic mixture according to the present invention.

The perfuming compounds comprise, preferably, between 7 and 15 carbon atoms.

According to an embodiment of the invention, the perfuming aldehyde or ketone has a molecular weight comprised between 100 and 220 g/mol and can be advantageously selected from the group consisting of an enal, an enone, an aldehyde comprising the moiety $CH_2CHO$ or CHMeCHO, an aromatic aldehyde or ketone (wherein the functional group is directly bound to an aromatic ring) and a cyclic or acyclic ketone (wherein the CO group is part or not of a cycle).

Furthermore, according to any of the embodiments mentioned above, the perfuming aldehyde or ketone is advantageously characterized by a vapor pressure above 2.0 Pa, as obtained by calculation using the software EPIwin v 3.10 (available at 2000 US Environmental Protection Agency). According to another embodiment the vapor pressure is above 5.0, or even above 7.0 Pa.

As mentioned further above, all these embodiments apply also in the case of the active ingredient being a flavoring, insect repellent or attractant, bactericide or fungicide ingredient.

More specifically, as non-limiting examples of the perfuming compounds in the embodiments mentioned above one may cite the following:
A) aldehydes of formula R"—CHO wherein R" is a linear or α-branched alkyl group of $C_6$ to $C_{12}$, benzaldehyde, 1,3-benzodioxol-5-carboxaldehyde(heliotropine), 3-(1,3-benzodioxol-5-yl)-2-methylpropanal, 2,4-decadienal, 2-decenal, 4-decenal, 8-decenal, 9-decenal, 3-(6,6-dimethylbicyclo[3.1.1]hept-2-en-2-yl)propanal, 2,4-dimethyl-3-cyclohexene-1-carbaldehyde (Triplal®, origin: International Flavors & Fragrances, New York, USA), 3,5-dimethyl-3-cyclohexene-1-carbaldehyde, 1-(3,3-dimethyl-1-cyclohexyl)-1-ethanone, 5,9-dimethyl-4,8-decadienal, 2,6-dimethyl-5-heptenal(melonal), 3,7-dimethyl-2,6-octadienal(citral), 3,7-dimethyloctanal, 3,7-dimethyl-6-octenal(citronellal), (3,7-dimethyl-6-octenyl)acetaldehyde, 3-dodecenal, 4-dodecenal, 3-ethoxy-4-hydroxybenzaldehyde(ethyl vanillin), 4-ethyl benzaldehyde, 3-(2 and 4-ethylphenyl)-2,2-dimethylpropanal, 2-furancarbaldehyde(furfural), 2,4-heptadienal, 4-heptenal, 2-hexyl-3-phenyl-2-propenal(hexylcinnamic aldehyde), 2-hydroxybenzaldehyde, 7-hydroxy-3,7-dimethyloctanal(hydroxycitronellal), 4-hydroxy-3-methoxybenzaldehyde(vanillin), 4- and 3-(4-hydroxy-4-methylpentyl)-3-cyclohexene-1-carbaldehyde (Lyral®, origin: International Flavors and Fragrances, New York, USA), 4-isopropylbenzaldehyde(cuminaldehyde), 3-(4-isopropylphenyl)-2-methylpropanal, 2-(4-isopropylphenyl)propanal, (4R)-1-p-menthene-9-carbaldehyde (Liminal®, origin: Firmenich SA, Geneva, Switzerland), 2- and 4-methoxybenzaldehyde(anis aldehyde), 6-methoxy-2,6-dimethylheptanal(methoxymelonal), 8(9)-methoxy-tricyclo[5.2.1.0.(2,6)]decane-3(4)-carbaldehyde (Scentenal®, origin: Firmenich SA, Geneva, Switzerland), 4-methylbenzaldehyde, 2-(4-methylenecyclohexyl)propanal, 1-methyl-4-(4-methyl-3-pentenyl)-3-cyclohexen-1-carbaldehyde (Precyclemone® B, origin: International Flavors & Fragrances, New York, USA), 4-(4-methyl-3-pentenyl)-3-cyclohexene-1-carbaldehyde (Acropal®, origin: Givaudan-Roure SA., Vernier, Switzerland), (4-methylphenoxy)acetaldehyde, (4-methylphenyl)acetaldehyde, 3-methyl-5-phenylpentanal, 2-(1-methylpropyl)-1-cyclohexanone, 2,4-nonadienal, 2,6-nonadienal, 2-nonenal, 6-nonenal, 8-nonenal, 2-octenal, phenoxyacetaldehyde, phenylacetaldehyde, 3-phenylbutanal (Trifernal®, origin: Firmenich SA, Geneva, Switzerland), 3-phenylpropanal, 2-phenylpropanal(hydratropaldehyde), 3-phenyl-2-propenal(cinnamic aldehyde), 3-(4-tert-butylphenyl)-2-methylpropanal (Lilial®, origin: Givaudan-Roure SA, Vernier, Switzerland), 3-(4-tert-butylphenyl)propanal (Bourgeonal®, origin: Quest International, Naarden, Netherlands), tricyclo[5.2.1.0(2,6)]decane-4-carbaldehyde, exo-tricyclo[5.2.1.0(2,6)]decane-8exo-carbaldehyde (Vertral®, origin: Symrise, Holzminden, Germany), 2,6,6-trimethyl-bicyclo[3.1.1]heptane-3-carbaldehyde(formyl pinane), 2,4,6- and 3,5,6-trimethyl-3-cyclohexene-1-carbaldehyde, 2,2,3-trimethyl-3-cyclopentene-1-acetaldehyde(campholenic aldehyde), 2,6,10-trimethyl-2,6,9,11-dodecatetraenal, 2,5,6-trimethyl-4-heptenal, 3,5,5-trimethylhexanal, 2,6,10-trimethyl-9-undecenal, 2-undecenal, 10-undecenal or 9-undecenal and their mixtures such as Intreleven aldehyde (origin: International Flavors & Fragrances, New York, USA), and B) $C_{6-11}$ ketones of formula R'—(CO)—R" wherein R' and R" are linear alkyl groups, damascenones and damascones, ionones and methyl ionones (such as Iralia® Total, origin: Firmenich SA, Geneva, Switzerland), irones, macrocyclic ketones such as, for example, cyclopentadecanone (Exaltone®) or 3-methyl-4-cyclopentadecen-1-one and 3-methyl-5-cyclopentadecen-1-one (Delta Muscenone) or 3-methyl-1-cyclopentadecanone (Muscone) all from Firmenich SA, Geneva, Switzerland, 1-(2-aminophenyl)-1-ethanone, 1-(5,5-dimethyl-1-cyclohexen-1-yl)-4-penten-1-one (Neobutenone®, origin: Firmenich SA, Geneva, Switzerland), 1-(3,3-dimethyl-1-cyclohexyl)-1-ethanone, 2,5-dimethyl-2-octene-6-one, 4,7-dimethyl-6-octene-3-one, (3,7-dimethyl-6-octenyloxy)acetaldehyde, 1-(2,4-dimethylphenyl)-1-ethanone, 4-(1,1-dimethylpropyl)-1-cyclohexanone (Orivone®, origin: International Flavors & Fragrances, New York, USA), 2,4-di-tert-butyl-1-cyclohexanone, ethyl 4-oxopentanoate, 1-(4-ethylphenyl)-1-ethanone, 2-hexyl-1-cyclopentanone, 2-hydroxy-3-methyl-2-cyclopenten-1-one, 4-(4-hydroxy-1-phenyl)-2-butanone (raspberry ketone), 1-(2- and 4-hydroxyphenyl)-1-ethanone, 4-isopropyl-2-cyclohexen-1-one, 1-(4-isopropyl-1-phenyl)-1-ethanone, 1(6),8-p-menthadien-2-one (carvone), 4(8)-p-menthen-3-one, 1-(1-p-menthen-2-yl)-1-propanone, menthone, (1R,4R)-8-mercapto-3-p-menthanone, 1-(4-methoxyphenyl)-1-ethanone, 7-methyl-2H,4H-1,5-benzodioxepin-3-one (Calone®, origin: C.A.L. SA, Grasse, France), 5-methyl-3-heptanone, 6-methyl-5-hepten-2-one, methyl 3-oxo-2-pentyl-1-cyclopentaneacetate (Hedione®, origin: Firmenich SA, Geneva, Switzerland), 1-(4-methylphenyl)-1-ethanone(4-methylacetophenone), 5-methyl-exo-tricyclo[6.2.1.0(2,7)]undecan-4-one, 3-methyl-4-(1,2,2-trimethylpropyl)-4-penten-2-one, 2-naphthalenyl-1-ethanone, 1-(octahydro-2,3,8,8-tetrame-2-naphthalenyl)-1-ethanone (isomeric mixture, Iso E Super®, origin: International Flavors & Fragrances, New York, USA), 3,4,5,6,6-pentamethyl-3-hepten-2-one, 2-pentyl-1-cyclopentanone (Delphone, origin: Firmenich SA, Geneva, Switzerland), 4-phenyl-2-butanone(benzylacetone), 1-phenyl-1-ethanone(acetophenone), 2- and 4-tert-butyl-1-cyclohexanone, 1-(4-tert-butylphenyl)-1-ethanone), 2,4,4,7-tetramethyl-6-octen-3-one, 1,7,7-trimethyl-bicyclo[2.2.1]heptan-2-one (camphor), 2,6,6-trimethyl-1-cycloheptanone, 2,6,6-trimethyl-2-cyclohexene-1,4-dione, 4-(2,6,6-trimethyl-2-cyclohexen-1-yl)-2-butanone(dihydroionone), 1-(2,4,4-trimethyl-2-cyclohexen-1-yl)-2-buten-1-one, 1-(3,5,6-trimethyl-3-cyclohexen-1-yl)-1-ethanone, 2,2,5-trimethyl-5-pentyl-1-cyclopentanone;

wherein the underlined compounds represent, in an embodiment of the invention, particularly useful fragrance aldehydes or ketones.

Furthermore, some of the above-mentioned compounds may also be used as perfuming, flavoring, insect repellent or attractant, bactericide or fungicide ingredients.

The invention's delivery system can be obtained by admixing together, in the presence of water, at least one compound of formula (I) and at least one perfuming compound. Furthermore, as it is very useful in the perfumery art to have compounded perfumery ingredients, so as to achieve more pleasant and natural scents, a delivery system obtained by reacting together at least two hydrazine derivatives with at least one perfuming compound is particularly appreciated. Similarly, it is also particularly appreciated to obtain a delivery system by reacting together at least one or two hydrazine derivatives with at least two, or even at least three, perfuming compounds.

As mentioned above, the invention's delivery system comprises several starting components that may react, in a reversible manner, between them to form addition products.

It is believed that the main components of the dynamic mixture are the free aldehyde, ketone, hydrazine derivative and the resulting addition products (such as hydrazones and the intermediate hemiaminal derivatives). A specific example of such a mixture and equilibrium is presented in Scheme (I):

Scheme (I):
Example of an equilibrium and the species present in a dynamic mixture composed of one specific aldehyde and one specific hydrazine derivative

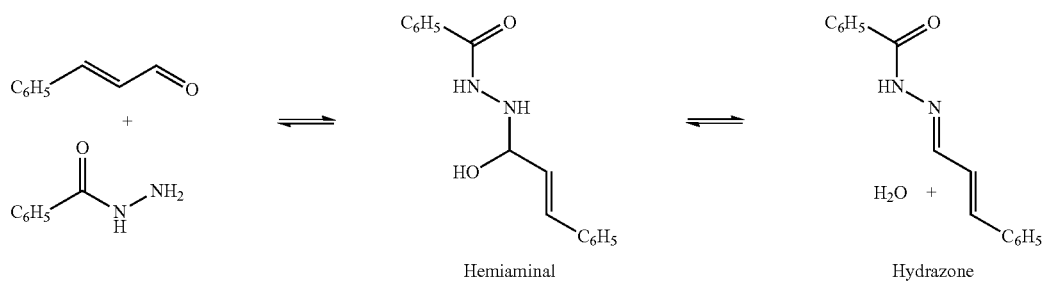

Hemiaminal         Hydrazone

As a consequence of the fact that the reactions are reversible, a dynamic mixture can also be obtained by adding one or more hydrazone derivatives into water and let the mixture attain its equilibrium. However, it has to be pointed out that the time required to reach the equilibrium point can vary significantly depending on the fact that there is used the hydrazone or the hydrazine derivative as starting material, as the time is believed to be dependent on various parameters such as solubilities or the basicity of the medium.

The preparation of the invention's dynamic mixture by the simple admixture of the perfuming compounds in the presence of water avoids the need of additional chemical steps such as the preparation of the hydrazones.

Therefore, due to its nature, the invention's dynamic mixture circumvents the problem of product instability observed with prior art precursors, by the fact that a dynamic equilibrium is spontaneously set up between these compounds. The equilibrium is stable during product storage as long as the consumer product parameters (such as concentration, temperature, pH or humidity, the presence of surfactant etc.) are kept constant. At given set of parameters, the time required to reach the equilibrium state mainly depends on the kinetic rate constant of the slowest step involved in the formation of the products of the equilibrium.

As mentioned above, the delivery system of the invention comprises various components. It is believed that, once the delivery system is deposited on a surface, the free perfuming aldehydes or ketones start to evaporate, diffusing in the surrounding environment their typical scent. The evaporation perturbs the chemical equilibrium and the various addition products start to decompose so as to restore the equilibrium. The consequence of such re-equilibration is the regeneration of free perfuming aldehydes or ketones, thus maintaining their concentration relatively constant over time and avoiding a too rapid evaporation.

Now, it has been observed that the various physical or thermodynamic properties of the delivery system, e.g. its deposition on a surface or the amount of addition products formed, can be influenced by the chemical nature of the perfuming compounds or of the hydrazine derivatives. Another way to influence the above-mentioned properties is to modify the molar ratio between the perfuming compounds and the hydrazine compounds. For instance, the lower the molar ratio between perfuming compounds and hydrazine derivatives, the longer takes the evaporation of all the perfuming compounds. The presence of other ingredients (such as surfactants, emulsifiers, gelators or others) typically used in the final consumer product formulation may also influence the above-mentioned properties.

Therefore, by varying the chemical structure of the mixture's constituents and their ratio, it is possible to fine-tune the release properties of the invention's dynamic mixture, so as to adapt its behavior to the specific requirement of the targeted consumer product.

According to the final application, a broad range for the speed of evaporation of the perfuming compound may be desirable.

The ratio between the total molar amount of perfuming aldehyde and/or ketone and the total molar amount of the compound of formula (I) can be comprised between 1:2 and 50:1, preferably between 1:1 and 10:1.

As previously mentioned, the invention's delivery system enables a controlled release of an active aldehyde or ketone, and in particular a perfuming one. Such a behavior makes the invention's dynamic mixture particularly suitable as active ingredient. Consequently, the use of an invention's delivery system as active ingredient is another object of the present invention. In particular it concerns a method to confer, enhance, improve or modify the odor properties of a perfuming composition or of a perfumed article, which method comprises adding to the composition or article an effective amount of an invention's delivery system.

Moreover, another object of the present invention concerns also a composition comprising the invention's delivery system. This concerns also in particular a perfuming composition comprising:

i) as perfuming ingredient, a delivery system as defined above;
ii) at least one ingredient selected from the group consisting of a perfumery carrier and a perfumery base; and
iii) optionally at least one perfumery adjuvant.

Preferably, in the perfuming composition the perfumery carrier, perfumery base and perfumery adjuvant have a total molar amount of aldehydes or ketones which is equal or higher than the molar amount of hydrazine derivatives of the delivery system.

By "perfumery carrier" we mean here a material which is practically neutral from a perfumery point of view, i.e. that does not significantly alter the organoleptic properties of perfuming ingredients. The carrier may be a liquid. As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as dipropyleneglycol, diethyl phthalate, isopropyl myristate, benzyl benzoate, 2-(2-ethoxyethoxy)-1-ethanol or ethyl citrate, which are the ones most commonly used.

Generally speaking, by "perfumery base" we mean here a composition comprising at least one perfuming co-ingredient.

The perfuming co-ingredient is not an aldehyde or ketone as defined above for the dynamic mixture. Moreover, by "perfuming co-ingredient" it is meant here a compound, which is used in perfuming preparation or composition to impart an hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of its general knowledge and according to intended use or application and the desired organoleptic effect. In general terms, these perfuming co-ingredients belong to chemical classes as varied as alcohols, esters, ethers, acetates, nitrites, terpene hydrocarbons, nitrogenous or sulphurous heterocyclic compounds and essential oils, and the perfuming co-ingredients can be of natural or synthetic origin. A further class of perfuming co-ingredient can be the aldehydes or ketones which do not react with the hydrazine derivative present in the dynamic mixture.

Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that the co-ingredients may also be compounds known to release in a controlled manner various types of perfuming compounds.

For the compositions which comprise both a perfumery carrier and a perfumery base, other suitable perfumery carrier, than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

Generally speaking, by "perfumery adjuvant" we mean here an ingredient capable of imparting additional added benefit such as a color, a particular light resistance, chemical stability and others. A detailed description of the nature and type of adjuvant commonly used in perfuming bases cannot be exhaustive, but it has to be mentioned that the ingredients are well known to a person skilled in the art.

An invention's composition consisting of an invention's delivery system and at least one perfumery carrier represents a particular embodiment of the invention as well as a perfuming composition comprising an invention's delivery system, at least one perfumery carrier, at least one perfumery base, and optionally at least one perfumery adjuvant.

As anticipated above, the invention's dynamic mixtures or compositions can be advantageously used for bringing a benefit to consumer products, such as its perfuming. Indeed, the mixture possesses several other properties that make it particularly suitable for this purpose. Consequently, a consumer article comprising the invention's delivery system is also an object of the present invention.

Indeed, and for example, another advantage of invention's mixture is an improved deposition on a surface of the perfuming aldehydes or ketones compared to those of the pure ketones or aldehydes as such.

All the above-mentioned properties, i.e. improved substantivity, prolonged time of evaporation, improved stability over aggressive agents, and improved deposition, are very important for a perfuming composition. Indeed, when the compositions are intended for use in fine perfumery, the invention's mixture may allow the creation of new perfuming effects which are otherwise difficult to be achieved, such as a fresh green note being present over several hours. In the case of perfuming compositions intended for the functional perfumery, the above-mentioned properties are also very important. For example, perfuming ingredients present as such in washing compositions which have generally little staying-power on a surface are consequently often eliminated, for example in the rinsing water or upon drying of the surface. This problem can be solved by using the invention's dynamic mixture, which possesses an improved stability over storage and substantivity on surfaces, such as textiles or hair.

Therefore, the mixtures according to the invention, owing to a lower and more uniform evaporation per unit of time, resulting in a controlled release of odoriferous molecules, can be incorporated in any application requiring the effect of prolonged liberation of an odoriferous component as defined hereinabove and furthermore can impart a fragrance and a freshness to a treated surface which will last well beyond the rinsing and/or drying processes. Suitable surfaces are, in particular, textiles, hard surfaces, hair and skin.

Consequently, the invention concerns also in particular consumer article in the form of a perfumed article comprising:
i) as perfuming ingredient, a delivery system as defined above; and
ii) a liquid consumer product base;
is also an object of the present invention.

Preferably, in perfumed articles the liquid consumer product base has a total molar amount of aldehydes and/or ketones which is equal or higher than the molar amount of hydrazine derivatives of the delivery system.

For the sake of clarity, it has to be mentioned that, by "liquid consumer product base" we mean here a consumer product which is compatible with a perfume or perfuming ingredients and which is not a solid, e.g. a more or less viscous solution, a suspension, an emulsion, a gel or a cream. In other words, a perfumed article according to the invention comprises the functional formulation, as well as optionally additional benefit agents, corresponding to a consumer product, e.g. a conditioner, a softener or an air freshener, and an olfactivly effective amount of an invention's dynamic mixture.

The nature and type of the constituents of the liquid consumer product base do not warrant a more detailed description here, which in any case would not be exhaustive, the skilled person being able to select them on the basis of its general knowledge and according to the nature and the desired effect of the article.

Suitable consumer products comprise liquid detergents and fabric softeners as well as all the other articles common in perfumery, namely perfumes, colognes or after-shave lotions, perfumed liquid soaps, shower or bath mousses, oils or gels, hygiene products or hair care products such as shampoos, body-care products, liquid based deodorants or antiperspirants, air fresheners comprising a liquid perfuming ingredient and also cosmetic preparations. As detergents are intended applications such as detergent compositions or cleaning products for washing up or for cleaning various surfaces, e.g. intended for textile, dish or hard-surface treatment, whether they are intended for domestic or industrial use. Other perfumed articles are fabric refreshers, ironing waters, papers, wipes or bleaches.

Preferred consumer products are perfumes, air fresheners, cosmetic preparations, softener bases or hair care products.

According to an embodiment of the invention, it is also possible to have a perfumed article comprising:
i) a hydrazine derivative of formula (I);
ii) a perfume or perfuming composition containing at least one perfuming aldehyde or ketone having a molecular weight comprised between 80 and 230 g/mol; and
iii) a solid consumer product base intended to be used in the presence of water.

In such a case, the invention's dynamic mixture will be formed once the consumer article is used by the consumer, since water will be present. Examples of such solid consumer product bases intended to be used in presence of water include powder detergents or "ready to use" powdered air fresheners.

Typical examples of fabric detergents or softener compositions into which the compounds of the invention can be incorporated are described in Ullman's Encyclopedia of Industrial Chemistry, vol. A8, pages 315-448 (1987) and vol. A25, pages 747-817 (1994); Flick, Advanced Cleaning Product Formulations, Noye Publication, Park Ridge, N.J. (1989); Showell, in Surfactant Science Series, vol. 71: Powdered Detergents, Marcel Dekker, New York (1988); Proceedings of the World Conference on Detergents (4th, 1998, Montreux, Switzerland), AOCS print.

Some of the above-mentioned articles may represent an aggressive medium for the invention's compounds, so that it may be necessary to protect the latter from premature decomposition, for example by encapsulation.

The proportions in which the delivery system according to the invention can be incorporated into the various aforementioned articles or compositions vary within a wide range of values. These values are dependent on the nature of the article or product to be perfumed and on the desired olfactory effect as well as the nature of the co-ingredients in a given composition when the dynamic mixtures according to the invention are mixed with perfuming co-ingredients, solvents or additives commonly used in the art.

For example, typical concentrations are in the order of 0.1% to 30% by weight, or even more, of the invention's delivery system based on the weight of the composition into which they are incorporated. Concentrations lower than these, such as in the order of 0.01% to 5% by weight, can be used when these delivery systems are applied directly in the perfuming of the various consumer products mentioned hereinabove.

Another object of the present invention relates to a method for the perfuming of a surface characterized in that the surface is treated in the presence of a dynamic mixture as defined above. Suitable surfaces are, in particular, textiles, hard surfaces, hair and skin.

Moreover, an additional aspect of the present invention is a method for prolonging the perfuming effect of a perfuming aldehyde or ketone, as defined above, characterized in that there is added at least one hydrazine derivative of formula (I), as defined above, to a perfuming composition containing at least one perfuming aldehyde or ketone, as defined above, and water. In other words, the use of a hydrazine derivative, as defined above, as additive to prolong the perfuming effect of a perfuming compositions containing at least one perfuming compound as defined above and water.

EXAMPLES

The invention will now be described in further detail by way of the following examples, wherein the abbreviations have the usual meaning in the art, the temperatures are indicated in degrees centigrade (° C.). If not stated otherwise, the NMR spectral data were recorded on a Bruker AMX 400 spectrometer in DMSO-$d_6$ at 400 MHz for $^1$H and at 100.6 MHz for $^{13}$C, the chemical displacement δ are indicated in ppm with respect to TMS as the standard, the coupling constants J are expressed in Hz. UV/Vis spectra were recorded in ethanol on a Perkin-Elmer Lambda 14 or Lambda 35 instrument, λ is given in nm (ε). Commercially available reagents and solvents were used without further purification if not stated otherwise. Reactions were carried out in standard glassware under $N_2$. The following hydrazine derivatives were obtained from commercial sources: benzohydrazide (1a, origin: Fluka), 2-furohydrazide (2a, origin: Fluka), 2-hydrazino-N,N,N-trimethyl-2-oxoethanaminium chloride (3a, Girard-T reagent, origin: Fluka), 1-(2-hydrazino-2-oxoethyl)pyridinium chloride (4a, Girard-P reagent, origin: Aldrich), ethyl hydrazinecarboxylate (5a, origin: Acros), N-phenylhydrazinecarboxamide (6a, origin: TCI), N-phenylhydrazinecarbothioamide (7a, origin: Acros), 4-methyl-1-benzenesulfonohydrazide (8a, origin: Acros), 4-hydrazinobenzoic acid (9a, origin: Acros), (1,1-dioxidotetrahydro-3-thienyl)hydrazine (10a, origin: Lanxess), 4H-1,2,4-triazol-4-amine (11a, origin: TCI), octanohydrazide (12a, caprylic hydrazide, origin: Fluka), terephthalohydrazide (13a, terephthalic dihydrazide, origin: TCI), hexanedihydrazide (14a, adipic dihydrazide, origin: Acros or Lanxess) and N',N'-bis(phenylmethylene)ethanedihydrazide (15b, oxalic bis(benzylidenehydrazide), origin: Aldrich). Other compounds were obtained as described below.

Although specific conformations or configurations are indicated for some of the compounds, this is not meant to limit the use of these compounds to the isomers described. According to the invention, all possible conformation or configuration isomers are expected to have a similar effect.

Non Commercial Hydrazine Derivatives Were Prepared as Follows:

Preparation of (2R,3R)-2,3-dihydroxysuccinohydrazide (16a)

A mixture of (+)-diethyl (R,R)-tartrate (5.00 g, 24.2 mmol) and hydrazine hydrate (51% in water, 5.9 ml=6.07 g, 96.7 mmol, origin: Acros) in ethanol (55 ml) was heated under reflux overnight. The formation of a white precipitate was observed. After cooling to room temperature, the reaction mixture was filtered, and the residue dried under vacuum to give 4.12 g (96%) of a white solid.

$^1$H-NMR: 8.78 (s, 2H); 5.38 (s br., 2H); 4.25 (s br., 4H); 2.50 (s, 2H).
$^{13}$C-NMR: 170.37 (s); 72.09 (d).

Preparation of (+)-(2R,3R)-2,3-bis(dodecyloxy)succinohydrazide (17a)

a) Preparation of (+)-(2R,3R)-2,3-bis(dodecyloxy)-N,N,N',N'-tetramethylsuccinamide Sodium hydride (3.60 g, 60%, 90.0 mmol) was washed with pentane (3×) before DMF (150 ml) and (+)-(2R,3R)-2,3-dihydroxy-N,N,N',N'-tetramethylsuccinamide (9.2 g, 45.0 mmol, origin: Aldrich) were added. The reaction mixture was left stirring at room temperature for 90 min, then a solution of 1-iodododecane (28.0 g, 94.5 mmol) in DMF (50 ml) was added. The reaction was left stirring for another 2 h at room temperature and then heated at 80° C. overnight. After cooling to room temperature, the reaction mixture was extracted with ether (4×), washed with water (2×), dried ($Na_2SO_4$), and concentrated. Column chromatography ($SiO_2$, dichloromethane/acetone 3:1) gave 5.93 g (28%) of a pale-yellow solid.

b) Preparation of (+)-(2R,3R)-2,3-bis(dodecyloxy)succinic acid

A suspension of the compound obtained under a) (6.63 g, 12.3 mmol), HCl (36%, 110 ml) and water (55 ml) was heated under reflux for 4 d. After cooling to room temperature, the reaction mixture was extracted with $CH_2Cl_2$ (3×), dried ($Na_2SO_4$), and concentrated to give 6.03 g (quant.) of the product.

c) Preparation of (+)-dimethyl (2R,3R)-2,3-bis(dodecyloxy)succinate

Ca. 1 ml of conc. sulfuric acid (55 drops) was added to a solution of the compound obtained under b) (4.18 g, 8.6 mmol) in methanol (275 ml). The reaction mixture was heated under reflux overnight. After cooling to room temperature, the product was concentrated and precipitated into 700 ml of water at 0° C. Filtration gave 3.98 g (90%) of a white solid.

d) Preparation of (+)-(2R,3R)-2,3-bis(dodecyloxy)succinohydrazide (17a)

A mixture of the compound obtained under c) (5.00 g, 9.7 mmol) and hydrazine hydrate (51% in water, 2.37 ml=2.44 g, 38.8 mmol) in ethanol (650 ml) was heated at reflux overnight. After cooling to room temperature, the reaction mixture was concentrated and filtered to give 2.76 g (55%) of a white solid.

$^1$H-NMR (CDCl$_3$): 7.82 (s, 2H); 4.34 (s, 2H); 3.87 (s br., 4H); 3.57-3.48 (m, 2H); 3.47-3.37 (m, 2H); 1.62-1.45 (m, 4H); 1.37-1.18 (m, 36H); 0.88 (t, J=6.9, 6H).
$^{13}$C-NMR (CDCl$_3$): 170.22 (s); 80.70 (d); 73.51 (t); 31.93 (t); 29.66 (t, 4×); 29.59 (t); 29.37 (t, 2×); 25.93 (t); 22.70 (t); 14.13 (q).

Preparation of
2-hydroxy-1,2,3-propanetricarbohydrazide (18a)

A mixture of trimethyl 2-hydroxy-1,2,3-propanetricarboxylate (1.00 g, 4.3 mmol, origin: Fluka) and hydrazine hydrate (51% in water, 1 ml=1.03 g, 16.7 mmol) in ethanol (20 ml) was heated under reflux overnight. The formation of a white precipitate was observed. After cooling to room temperature, the reaction mixture was filtered, and the residue dried under vacuum to give 0.85 g (85%) of a white solid.
$^1$H-NMR: 9.09 (s br., 2H); 8.90 (s br., 1H); 6.15 (s br., 1H); 4.21 (s br., 6H); 2.47 (AB, J=14.3, 5.1, 4H).
$^{13}$C-NMR: 172.38 (s); 168.93 (s); 74.50 (s); 40.64 (t).

Preparation of (±)-poly(acrylohydrazide) (19a)

Poly(methyl acrylate) in toluene (origin: Aldrich, $M_w$=30700, $M_n$=10600) was concentrated. Hydrazine hydrate (51% in water, 68 ml=69.90 g, 1112.4 mmol) was added to 7.00 g (81.3 mmol) of the polymer and the mixture heated at 80° C. for 5 h. After cooling to room temperature, the reaction mixture was poured into 700 ml of methanol, and the white precipitate was filtered. The solid was suspended in dichloromethane (1×) and ether (2×) (upon sonication) to remove remaining methanol and finally gave 3.52 g (50%) of a white solid.
$^1$H-NMR (D$_2$O): 2.5-1.0 (m, 3H).
$^{13}$C-NMR (D$_2$O): 177.84 (s); 43.42 (d); 37.38 (t br.).

Preparation of poly((1→4)-6-hydrazino-α-D-galacto-hexodialdo-1,5-pyranose) (20a)

Pectin (from apples, 20.00 g, origin: Fluka) was suspended in 250 ml of water and stirred mechanically for 1 h, before hydrazine hydrate (51% in water, 17.6 ml=18.09 g) was added during 5 min. The reaction mixture was left stirring at room temperature for 3 h, then at 30° C. for another 140 h. The crude product was washed with toluene. After decantation of the toluene, the remaining product was dried under reduced pressure and lyophilized overnight to give 21.5 g of a solid.
$^{13}$C-NMR analysis (0.1 M NaOH in D$_2$O) showed the disappearance of the peak at 51.75 corresponding to the methyl ester group in pectin.
Non Commercial Hydrazone Derivatives Were Prepared as Follows:

Preparation of
N'-[(1E)-phenylmethylene]benzohydrazide (1b)

A mixture of 1a (3.00 g, 22.0 mmol) and benzaldehyde (3.50 g, 33.0 mmol) in ethanol (50 ml) was heated under reflux for 3 h. After cooling to room temperature, the mixture was filtered, and the residue washed with ethanol and dried under vacuum to give 4.18 g (85%) of a white solid.
UV/Vis (ethanol): 299 (28600), 294 (sh, 28500), 281 (sh, 22600), 224 (sh, 17500), 219 (18900), 205 (sh, 25900), 202 (29700).
$^1$H-NMR: 11.90 (s, 1H); 8.51 (s, 1H); 7.96 (d, J=7.7, 2H); 7.76 (d, J=6.1, 2H); 7.66-7.37 (m, 6H).
$^{13}$C-NMR: 163.09 (s); 147.73 (d); 134.28 (s); 133.38 (s); 131.67 (d); 129.99 (d); 128.76 (d); 128.39 (d); 127.55 (d); 127.02 (d).

Preparation of N'-[(1E,2E)-3-phenyl-2-propenylidene]benzohydrazide (1c)

A mixture of 1a (3.00 g, 22.0 mmol) and trans cinnamic aldehyde (4.35 g, 32.9 mmol, origin: Aldrich) in hexane (100 ml) was stirred at room temperature for 2 h. The reaction mixture was filtered, the residue washed with hexane and dried under vacuum to give 4.95 g (90%) of a white solid.
UV/Vis (ethanol): 345 (sh, 21500), 322 (44700), 317 (44400), 239 (sh, 15600), 230 (19400), 224 (sh, 18400).
$^1$H-NMR (CDCl$_3$): 9.36 (s br., 1H); 8.10-7.99 (m, 1H); 7.91-7.79 (m, 2H); 7.58-7.49 (m, 1H); 7.49-7.40 (m, 4H); 7.39-7.27 (m, 3H); 7.17-7.03 (m, 1H); 6.90 (d, J=15.9, 1H).
$^{13}$C-NMR (CDCl$_3$): 164.11 (s); 149.77 (d); 140.29 (d); 135.71 (s); 133.03 (s); 132.14 (d); 129.20 (d); 128.89 (d); 128.79 (d); 127.32 (d); 127.15 (d); 125.00 (d).

Preparation of
N'-[(1E)-3-phenylbutylidene]benzohydrazide (1d)

A mixture of 1a (1.50 g, 11.0 mmol) and 3-phenylbutanal (Trifernal®, 2.45 g, 16.5 mmol) in ethanol (28 ml) was heated under reflux for 2 h. After cooling to room temperature, the reaction mixture was concentrated in vacuo. The product was washed with ethanol, then with hexane and finally dried under vacuum (0.17 mbar) to give 2.04 g (70%) of a white solid.
UV/Vis (ethanol): 253 (20200), 238 (sh, 17000), 230 (sh, 16200).
$^1$H-NMR: 11.43 (s, 1H); 7.84 (d, J=7.2, 2H); 7.65 (t, J=5.4, 1H); 7.55 (t, J=7.2, 1H); 7.48 (t, J=7.4, 2H); 7.37-7.26 (m, 4H); 7.24-7.17 (m, 1H); 3.09-2.96 (m, 1); 2.65-2.48 (m, 2H); 1.26 (d, J=7.2, 3H).
$^{13}$C-NMR: 162.63 (s); 150.90 (d); 145.89 (s); 133.39 (s); 131.43 (d); 128.35 (d); 128.25 (d); 127.40 (d); 126.82 (d); 126.08 (d); 40.11 (t); 37.25 (d); 21.88 (q).

Preparation of
N'-[(1E)-10-undecenylidene]benzohydrazide (1e)

A mixture of 1a (1.50 g, 11.0 mmol) and 10-undecenal (2.80 g, 16.5 mmol) in ethanol (28 ml) was heated under reflux for 2 h. After cooling to room temperature, the product was concentrated, washed with hexane and dried under vacuum (0.20 mbar) to give 2.78 g (88%) of a white solid.
UV/Vis (ethanol): 250 (23500), 239 (sh, 20500), 229 (sh, 18200), 204 (sh, 31100), 203 (32700).
$^1$H-NMR: 11.40 (s, 1H); 7.84 (d, J=7.7, 2H); 7.74 (t, J=5.3, 1H); 7.56 (t, J=7.2, 1H); 7.49 (t, J=7.4, 2H); 5.86-5.73 (m, 1H); 5.04-4.89 (m, 2H); 2.25 (q, J=6.5, 2H); 2.01 (q, J=6.8, 2H); 1.55-1.42 (m, 2H); 1.41-1.15 (m, 10H).
$^{13}$C-NMR: 162.65 (s); 152.19 (d); 138.72 (d); 133.53 (s); 131.39 (d); 128.27 (d); 127.38 (d); 114.53 (t); 33.09 (t); 31.90 (t); 28.69 (t, 2×); 28.56 (t); 28.40 (t); 28.18 (t); 25.95 (t).

Preparation of
N'-[(1E)-phenylmethylene]-2-furohydrazide (2b)

A mixture of 2a (3.00 g, 23.8 mmol) and benzaldehyde (3.78 g, 35.6 mmol) in ethanol (50 ml) was heated under reflux for 3 h. After cooling to room temperature, the mixture was filtered, and the residue washed with ethanol and dried under vacuum to give 4.74 g (92%) of a white solid.

UV/Vis (ethanol): 359 (sh, 1300), 304 (33800), 256 (sh, 11800), 225 (sh, 15900), 218 (sh, 18900), 213 (18800), 205 (sh, 21400), 202 (22900).

$^1$H-NMR: 11.86 (s, 1H); 8.48 (s, 1H); 7.96 (s, 1H); 7.79-7.68 (m, 2H); 7.52-7.41 (m, 3H); 7.33 (s, 1H); 6.72 (s, 1H).

$^{13}$C-NMR: 154.15 (s); 147.78 (d); 146.56 (s); 145.77 (d); 134.17 (s); 130.00 (d); 128.77 (d); 126.99 (d); 114.86 (d); 112.00 (d).

Preparation of N'-[(1E,2E)-3-phenyl-2-propenylidene]-2-furohydrazide (2c)

A mixture of 2a (2.00 g, 15.9 mmol) and trans cinnamic aldehyde (3.14 g, 23.7 mmol) in hexane (75 ml) was heated at 60° C. for 2 h. After cooling to room temperature, the mixture was filtered, and the residue dried under vacuum to give 3.51 g (92%) of a yellow solid.

UV/Vis (ethanol): 347 (sh, 26700), 330 (46400), 321 (45600), 304 (sh, 31200), 265 (13100), 237 (sh, 11900), 230 (13900), 225 (13900).

$^1$H-NMR: 11.78 (s, 1H); 8.33-8.19 (m, 1H); 7.95 (s, 1H); 7.63 (d, J=7.2, 2H); 7.40 (t, J=7.4, 2H); 7.34 (d, J=7.2, 1H); 7.37-7.25 (m, 1H); 7.16-7.00 (m, 2H); 6.73-6.68 (m, 1H).

$^{13}$C-NMR: 153.98 (s); 149.74 (d); 146.60 (s); 145.69 (d); 138.96 (d); 135.81 (s); 128.73 (d, 2×); 127.00 (d); 125.54 (d); 114.86 (d); 112.00 (d).

Preparation of N'-[(1E)-(4-hydroxy-3-methoxyphenyl)methylene]-2-furohydrazide (2d)

A mixture of 2a (1.50 g, 11.9 mmol) and vanillin (2.71 g, 17.8 mmol) in ethanol (30 ml) was heated under reflux for 2 h. After cooling to room temperature, the mixture was filtered, and the residue washed with hexane and dried under vacuum (0.24 mbar) to give 2.49 g (80%) of a white solid still containing some ethanol.

UV/Vis (ethanol): 384 (sh, 2300), 337 (sh, 39600), 333 (sh, 42100), 330 (42400), 319 (sh, 36500), 301 (30100), 289 (29900), 278 (sh, 28300), 265 (29200), 239 (sh, 22200), 229 (sh, 20400), 202 (29100).

$^1$H-NMR: 11.67 (s, 1H); 9.56 (s, 1H); 8.34 (s, 1H); 7.93 (s, 1H); 7.29 (d, J=7.7, 2H); 7.08 (d, J=7.7, 1H); 6.85 (d, J=8.2, 1H); 6.70 (s, 1H); 3.84 (s, 3H).

$^{13}$C-NMR: 153.92 (s); 148.94 (s); 148.36 (s); 147.94 (d); 146.71 (s); 145.53 (d); 125.54 (s); 122.11 (d); 115.35 (d); 114.46 (d); 111.91 (d); 108.83 (d); 55.46 (q).

Preparation of N'-[(3R)-3,7-dimethyl-6-octenylidene]-2-furohydrazide (2e)

A mixture of 2a (1.50 g, 11.9 mmol) and (R)-citronellal (2.74 g, 17.7 mmol) in ethanol (30 ml) was heated under reflux for 2 h. After cooling to room temperature, the product was concentrated and the excess of citronellal removed by Kugelrohr distillation (120° C., 0.39 mbar) to give 2.03 g (55%) of a yellow solid as a mixture of two isomers (ca. 7:1).

UV/Vis (ethanol): 330 (sh, 420), 267 (27300), 251 (sh, 20700), 241 (sh, 15400), 232 (sh, 11000), 211 (sh, 11500), 202 (14300).

$^1$H-NMR (CDCl$_3$, major isomer): 9.49 (s, 1H); 7.59 (t, J=5.1, 1H); 7.45 (s, 1H); 7.26 (s br., 1H); 6.54-6.49 (m, 1H); 5.07 (t, J=7.2, 1H); 2.47-2.35 (m, 1H); 2.32-2.18 (m, 1H); 2.13-2.90 (m, 2H); 1.82-1.71 (m, 1H); 1.68 (s, 3H); 1.60 (s, 3H); 1.48-1.33 (m, 1H); 1.33-1.18 (m, 1H); 0.95 (d, J=6.7, 3H);

$^{13}$C-NMR (CDCl$_3$, major isomer): 154.48 (s); 152.21 (d); 146.70 (s); 144.29 (d); 131.58 (s); 124.28 (d); 115.81 (d); 112.33 (d); 39.45 (t); 36.86 (t); 31.20 (d); 25.71 (q); 25.44 (t); 19.54 (q); 17.68 (q).

Preparation of N,N,N-trimethyl-2-oxo-2-{(2E)-2-[(2E)-3-phenyl-2-propenylidene]-hydrazino}ethanaminium chloride (3c)

A mixture of 3a (0.82 g, 4.9 mmol) and trans cinnamic aldehyde (0.5 g, 3.8 mmol) in ethanol (12 ml) was heated under reflux for 1 h. After cooling to room temperature, the mixture was filtered, and the residue dried under vacuum to give 0.32 g (30%) of a white solid consisting of two isomers with respect to the amide bond conformation (E:Z ca. 2:1).

UV/Vis (ethanol): 361 (sh, 2200), 332 (sh, 21800), 311 (44700), 303 (sh, 42500), 240 (sh, 8700), 233 (12200), 224 (sh, 11100).

$^1$H-NMR (major isomer): 12.25 (s br., 1H); 7.95 (d, J=9.2, 1H); 7.68-7.58 (m, 2H); 7.44-7.31 (m, 3H); 7.11 (d, J=16.4, 1H); 6.93 (dd, J=16.4, 9.2, 1H); 4.70 (s, 2H); 3.32 (s, 9H);

(minor isomer): 8.35 (s, 1H); 8.17 (d, J=9.2, 1H); 7.68-7.58 (m, 2H); 7.44-7.31 (m, 3H); 7.12 (d, J=16.4, 1H); 7.01 (dd, J=16.4, 9.2, 1H); 4.36 (s, 2H); 3.28 (s, 9H).

$^{13}$C-NMR (major isomer): 164.95 (s); 147.85 (d); 140.29 (d); 135.48 (s); 129.04 (d); 128.79 (d); 127.09 (d); 124.19 (d); 62.12 (t); 53.09 (q);

(minor isomer): 159.60 (s); 150.64 (d); 140.29 (d); 135.57 (s); 129.04 (d); 128.74 (d); 127.15 (d); 124.87 (d); 63.17 (t); 53.34 (q).

Preparation of 1-{2-[(2E)-2-benzylidenehydrazino]-2-oxoethyl}pyridinium chloride (4b)

A mixture of 4a (3.00 g, 16.0 mmol) and benzaldehyde (2.54 g, 23.9 mmol) in ethanol (45 ml) was heated under reflux for 3 h. After cooling to room temperature, the mixture was filtered, and the residue washed with ethanol. Recrystallization of the filtrate and drying under high vacuum gave a total of 4.28 g (97%) of a white solid consisting of two isomers with respect to the amide bond conformation (E:Z ca. 4:1).

UV/Vis (ethanol): 299 (sh, 15500), 289 (sh, 23300), 281 (25400), 275 (sh, 24600), 268 (sh, 22800), 223 (sh, 15800), 217 (20000), 213 (sh, 19000), 206 (sh, 17400).

$^1$H-NMR (major isomer): 12.38 (s, 1H); 9.14 (d, J=5.1, 2H); 8.71 (t, J=7.7, 1H); 8.32-8.20 (m, 2H); 8.26 (s, 1H); 7.80-7.73 (m, 2H); 7.53-7.42 (m, 3H); 6.11 (s, 2H);

(minor isomer): 13.18 (s, 1H); 9.14 (d, J=5.1, 2H); 8.74-8.66 (m, 1H); 8.46 (s, 1H); 8.32-8.20 (m, 2H); 7.73-7.67 (m, 2H); 7.53-7.42 (m, 3H); 5.74 (s, 2H).

$^{13}$C-NMR (major isomer): 166.40 (s); 146.40 (d); 146.12 (d); 145.05 (d); 133.63 (s); 130.20 (d); 128.79 (d); 127.43 (d); 126.90 (d); 61.33 (t);

(minor isomer): 161.28 (s); 147.88 (d); 146.26 (d); 146.12 (d); 133.78 (s); 130.20 (d); 128.79 (d); 127.43 (d); 127.04 (d); 60.85 (t).

Preparation of 1-(2-oxo-2-{(2E)-2-[(2E)-3-phenyl-2-propenylidene]hydrazino}ethyl)-pyridinium chloride (4c)

A mixture of 4a (1.5 g, 8.0 mmol) and trans cinnamic aldehyde (1.6 g, 12.0 mmol) in ethanol (20 ml) was heated under reflux for 3 h. After cooling to room temperature, the mixture was filtered, and the residue dried under vacuum (0.6 mbar) to give 0.51 g (21%) of a pale-yellow solid consisting of two isomers with respect to the amide bond conformation (E:Z ca. 3:1).

UV/Vis (ethanol): 360 (sh, 1900), 325 (sh, 30000), 310 (43400), 303 (sh, 41900), 268 (14600), 262 (sh, 12700), 239 (sh, 14200), 231 (17200), 225 (sh, 16300).

$^1$H-NMR (major isomer): 12.22 (s, 1H); 9.12 (d, J=6.1, 2H); 8.75-8.65 (m, 1H); 8.24 (t, J=6.9, 2H); 8.06 (d, J=9.2, 1H); 7.70-7.59 (m, 2H); 7.46-7.30 (m, 3H); 7.18-6.93 (m, 2H); 5.95 (s, 2H);

(minor isomer): 13.01 (s, 1H); 9.12 (d, J=6.1, 2H); 8.75-8.65 (m, 1H); 8.24 (t, J=6.9, 2H); 8.23-8.18 (m, 1H); 7.70-7.59 (m, 2H); 7.46-7.30 (m, 3H); 7.18-6.93 (m, 2H); 5.70 (s, 2H).

$^{13}$C-NMR (major isomer): 166.03 (s); 147.69 (d); 146.41 (d); 146.07 (d); 139.97 (d); 135.54 (s); 128.99 (d); 128.77 (d); 127.38 (d); 127.10 (d); 124.38 (d); 61.25 (t);

(minor isomer): 161.08 (s); 150.03 (d); 146.24 (d); 146.12 (d); 139.86 (d); 135.64 (s); 128.90 (d); 128.73 (d); 127.46 (d); 127.10 (d); 125.03 (d); 60.82 (t).

Preparation of ethyl (2E)-2-benzylidenehydrazinecarboxylate (5b)

A mixture of 5a (3.00 g, 28.8 mmol) and benzaldehyde (4.60 g, 43.3 mmol) in ethanol (85 ml) was heated under reflux for 3 h. After cooling to room temperature, the mixture was filtered, and the residue washed with ethanol and dried under vacuum to give 4.82 g (87%) of a white solid.

UV/Vis (ethanol): 332 (sh, 300), 298 (sh, 12600), 290 (sh, 18900), 279 (24400), 272 (sh, 23300), 221 (sh, 14500), 216 (19400), 211 (19200), 207 (18700).

$^1$H-NMR: 11.11 (s, 1H); 8.03 (s, 1H); 7.66-7.59 (m, 2H); 7.46-7.35 (m, 3H); 4.15 (q, J=7.0, 2H); 1.24 (t, J=6.9, 3H).

$^{13}$C-NMR: 153.38 (s); 143.68 (d); 134.33 (s); 129.43 (d); 128.66 (d); 126.50 (d); 60.40 (t); 14.46 (q).

Preparation of ethyl 2-[(1E,2E)-3-phenyl-2-propenylidene]hydrazinecarboxylate (5c)

A mixture of 5a (4.00 g, 38.4 mmol) and trans cinnamic aldehyde (7.60 g, 57.5 mmol) in ethanol (100 ml) was heated under reflux for 3 h. After cooling to room temperature, the mixture was filtered, and the residue dried under vacuum to give 6.77 g of a white solid. Refiltration of the filtrate gave another 0.73 g of the residue and an overall yield of 91%.

UV/Vis (ethanol): 322 (sh, 24400), 307 (34400), 282 (sh, 20200), 237 (sh, 8700), 230 (12500), 225 (12000).

$^1$H-NMR: 11.02 (s br., 1H); 7.83 (d, J=8.2, 1H); 7.56 (d, J=7.2, 2H); 7.38 (t, J=7.4, 2H); 7.30 (t, J=7.4, 1H); 6.98 (dd, J=15.9, 8.7, 1H); 6.91 (d, J=15.9, 1H); 4.14 (q, J=7.0, 2H); 1.23 (t, J=6.9, 3H).

$^{13}$C-NMR: 153.32 (s); 145.89 (d); 137.40 (s); 135.95 (d); 128.69 (d); 128.48 (d); 126.83 (d); 125.48 (d); 60.39 (t); 14.46 (q).

Preparation of benzaldehyde N-phenylsemicarbazone (6b)

A mixture of 6a (3.00 g, 19.8 mmol) and benzaldehyde (3.16 g, 29.8 mmol) in ethanol (45 ml) was heated under reflux for 3 h. After cooling to room temperature, the mixture was filtered, and the residue washed with ethanol and dried under vacuum. Recrystallization of the filtrate gave a total of 4.13 g (87%) of a white solid.

UV/Vis (ethanol): 309 (sh, 18800), 294 (27300), 287 (sh, 25900), 276 (sh, 19600), 239 (sh, 20100), 232 (22700), 222 (sh, 20200), 202 (34200).

$^1$H-NMR: 10.75 (s, 1H); 8.90 (s, 1H); 7.96 (s, 1H); 7.88-7.82 (m, 2H); 7.67 (d, J=7.7, 2H); 7.48-7.36 (m, 3H); 7.30 (t, J=7.9, 2H); 7.02 (t, J=7.4, 1H).

$^{13}$C-NMR: 152.96 (s); 140.68 (d); 138.97 (s); 134.29 (s); 129.31 (d); 128.49 (d); 128.33 (d); 126.93 (d); 122.38 (d); 119.80 (d).

Preparation of (1E,2E)-3-phenylacrylaldehyde N-phenylsemicarbazone (6c)

A mixture of 6a (2.00 g, 13.2 mmol) and trans cinnamic aldehyde (2.60 g, 19.7 mmol) in ethanol (35 ml) was heated under reflux for 2.5 h. After cooling to room temperature, the mixture was filtered, and the residue dried under vacuum to give 2.89 g (84%) of a pale-yellow solid.

UV/Vis (ethanol): 333 (sh, 30800), 317 (44300), 304 (sh, 37000), 241 (sh, 21300), 236 (22600), 225 (sh, 16400).

$^1$H-NMR: 10.72 (s, 1H); 8.80 (s, 1H); 7.81 (d, J=7.7, 1H); 7.65 (d, J=7.7, 2H); 7.56 (d, J=7.7, 2H); 7.46-7.35 (m, 2H); 7.35-7.25 (m, 3H); 7.10-6.92 (m, 3H).

$^{13}$C-NMR: 152.74 (s); 142.84 (d); 139.04 (s); 136.97 (d); 136.01 (s); 128.79 (d); 128.46 (d); 128.39 (d); 126.67 (d); 125.39 (d); 122.24 (d); 119.20 (d).

Preparation of 4-methyl-N'-[(1E)-phenylmethylene] benzenesulfonohydrazide (8b)

A mixture of 8a (3.00 g, 16.1 mmol) and benzaldehyde (2.56 g, 24.1 mmol) in ethanol (38 ml) was heated under reflux for 3 h. After cooling to room temperature, the mixture was filtered, and the residue washed with ethanol and dried under vacuum. Recrystallization of the filtrate gave a total of 3.59 g (81%) of a white solid.

UV/Vis (ethanol): 331 (sh, 1700), 297 (sh, 11300), 288 (sh, 16900), 278 (20600), 272 (sh, 20200), 266 (sh, 18400), 259 (sh, 14900), 221 (sh, 22900), 215 (sh, 27000), 205 (sh, 33400), 202 (35900).

$^1$H-NMR: 11.47 (s, 1H); 7.93 (s, 1H); 7.79 (d, J=8.7, 2H); 7.60-7.53 (m, 1H); 7.45-7.35 (m, 5H); 2.35 (s, 3H).

$^{13}$C-NMR: 146.88 (d); 143.35 (s); 136.08 (s); 133.59 (s); 129.97 (d); 129.57 (d); 128.69 (d); 127.15 (d); 126.66 (d); 20.90 (q).

Preparation of 4-methyl-N'-[(1E)-1-phenylethylidene]benzenesulfonohydrazide (8d)

A mixture of 8a (3.00 g, 16.1 mmol) and 1-phenyl-1-ethanone(acetophenone, 2.90 g, 24.1 mmol) in ethanol (45 ml) was heated under reflux for 4 h. After cooling to room temperature, the mixture was filtered, and the residue washed with ethanol and dried under vacuum (0.10 mbar) to give 2.84 g (61%) of a white solid.

UV/Vis (ethanol): 276 (sh, 10900), 270 (sh, 12200), 264 (12500), 258 (sh, 12000), 229 (sh, 15400), 220 (sh, 19500), 214 (sh, 21000), 202 (29100).

$^1$H-NMR: 10.51 (s, 1H); 7.82 (d, J=8.2, 2H); 7.66-7.59 (m, 2H); 7.41 (d, J=8.2, 2H); 7.39-7.33 (m, 3H); 2.36 (s, 3H); 2.18 (s, 3H).

$^{13}$C-NMR: 153.04 (s); 143.23 (s); 137.32 (s); 136.16 (s); 129.35 (d); 129.26 (d); 128.25 (d); 127.47 (d); 125.85 (d); 20.91 (q); 14.17 (q).

Preparation of 4-[(2E)-2-benzylidenehydrazino]benzoic acid (9b)

A mixture of 9a (3.00 g, 19.7 mmol) and benzaldehyde (3.14 g, 29.6 mmol) in ethanol (50 ml) was heated under reflux for 3 h. After cooling to room temperature, the mixture was filtered, and the residue washed with ethanol and dried under vacuum (0.21 mbar) to give 2.14 g (45%) of a pale-yellow solid.

UV/Vis (ethanol): 365 (sh, 41400), 353 (47800), 308 (sh, 13100), 297 (sh, 11200), 278 (8500), 236 (18700), 229 (sh, 16400), 203 (sh, 29500), 201 (31600).

$^1$H-NMR: 12.31 (s br., 1H); 10.82 (s, 1H); 7.96 (s, 1H); 7.83 (d, J=8.7, 2H); 7.70 (d, J=7.7, 2H); 7.41 (t, J=7.7, 2H); 7.34 (t, J=7.4, 1H); 7.12 (d, J=8.7, 2H).

$^{13}$C-NMR: 167.20 (s); 148.72 (s); 138.88 (d); 135.19 (s); 131.11 (d); 128.60 (d); 128.45 (d); 125.94(d); 120.28(s); 111.10 (d).

Preparation of N'-[(1E)-3,5,5-trimethylhexylidene]octanohydrazide (12d)

A mixture of 12a (3.00 g, 19.0 mmol) and 3,5,5-trimethylhexanal (4.05 g, 28.4 mmol) in ethanol (48 ml) was heated under reflux for 2 h. After cooling to room temperature, the product was concentrated and washed with ethanol. Drying under high vacuum (0.33 mbar) gave a total of 4.69 g (88%) of a colorless oil consisting of two isomers with respect to the amide bond conformation (E:Z ca. 56:44).

UV/Vis (ethanol): 231 (11700), 213 (sh, 8900).

$^1$H-NMR (major isomer): 10.72 (s, 1H); 7.27 (t, J=5.8, 1H); 2.49-2.38 (m, 2H); 2.22-2.18 (m, 2H); 1.80-1.69 (m, 1H); 1.57-1.46 (m, 2H); 1.32-1.18 (m, 9H); 1.10-0.99 (m, 1H); 0.94 (s, 3H); 0.90-0.82 (m, 6H); 0.87 (s, 9H);

(minor isomer): 10.86 (s, 1H); 7.43 (t, J=5.9, 1H); 2.22-2.18 (m, 4H); 1.80-1.69 (m, 1H); 1.57-1.46 (m, 2H); 1.32-1.18 (m, 9H); 1.10-0.99 (m, 1H); 0.92 (s, 3H); 0.90-0.82 (m, 6H); 0.88 (s, 9H).

$^{13}$C-NMR (major isomer): 173.64 (s); 145.84 (d); 49.69 (t); 40.93 (t); 31.79 (t); 31.07 (t); 30.75 (s); 29.71 (q); 28.60 (t); 28.34 (t); 27.23 (d); 24.23 (t); 22.51 (q); 21.98 (t); 13.84 (q);

(minor isomer): 167.99 (s); 149.15 (d); 49.86 (t); 41.09 (t); 33.95 (t); 31.09 (t); 30.77 (s); 29.71 (q); 28.52 (t); 28.34 (t); 27.31 (d); 24.92 (t); 22.48 (q); 21.98 (t); 13.84 (q).

Preparation of N',N'-bis[(1E)-phenylmethylene]hexanedihydrazide (14b)

A suspension of 14a (4.00 g, 22.9 mmol) and benzaldehyde (7.30 g, 68.9 mmol) in ethanol (95 ml) was heated under reflux for 4 h. After cooling to room temperature, the mixture was filtered, and the residue dried under vacuum to give 7.86 g (98%) of a white solid as a mixture of three isomers with respect to the amide bond conformation (E/Z:E/E:Z/Z ca. 1.4:1.1:1).

UV/Vis (ethanol): 300 (sh, 30000), 290 (sh, 44100), 283 (46000), 274 (sh, 40500), 224 (sh, 26700), 218 (34400), 213 (sh, 31300), 207 (sh, 27400).

$^1$H-NMR (major isomer): 11.37 (s, 1H); 11.24 (s, 1H); 8.18 (s, 1H); 7.99 (s, 1H); 7.80-7.57 (m, 4H); 7.52-7.32 (m, 6H); 2.77-2.60 (m, 2H); 2.32-2.18 (m, 2H); 1.76-1.66 (m, 4H).

$^{13}$C-NMR (major isomer): 174.10 (s); 168.41 (s); 145.66 (d); 142.36 (d); 134.30 (s); 134.26 (s); 129.73 (d); 129.49 (d); 128.67 (d, 2x); 126.84 (d); 126.49 (d); 33.99 (t); 31.60 (t); 24.73 (t); 23.82 (t).

Preparation of N',N'-bis[(1E)-(4-hydroxy-3-methoxyphenyl)methylene]hexanedihydrazide (14d)

A suspension of 14a (4.00 g, 22.9 mmol) and vanillin (10.48 g, 68.9 mmol.) in ethanol (80 ml) was heated under reflux for 5 h. After cooling to room temperature, the mixture was filtered, and the residue dried under vacuum to give 10.03 g (99%) of a white solid as a mixture of three isomers with respect to the amide bond conformation (E/Z:E/E:Z/Z ca. 2:1:1).

UV/Vis (ethanol): 327 (sh, 37700), 316 (45900), 292 (37700), 282 (sh, 31900), 234 (sh, 30400), 227 (34400), 220 (sh, 33700), 201 (29000).

$^1$H-NMR (major isomer): 11.16 (s, 1H); 11.06 (s, 1H); 9.46 (s br., 2H); 8.04 (s, 1H); 7.87 (s, 1H); 7.28-7.19 (m, 2H); 7.08-7.00 (m, 2H); 6.85-6.76 (m, 2H); 3.81 (s, 6H); 2.72-2.58 (m, 2H); 2.28-2.13 (m, 2H); 1.72-1.54 (m, 4H).

$^{13}$C-NMR (major isomer): 173.81 (s); 168.09 (s); 148.66 (s); 148.39 (s); 147.88 (s); 147.80 (s); 146.24 (d); 142.80 (d); 125.71 (s); 126.66 (s); 121.78 (d); 120.75 (d); 115.43 (d); 115.28 (d); 109.18 (d); 108.81 (d); 55.42 (q); 33.98 (t); 31.68 (t); 24.77 (t); 24.15 (t).

Preparation of N',N'-bis[(1E)-1-methyl-3-phenylpropylidene]hexanedihydrazide (14e)

A mixture of 14a (1.50 g, 8.6 mmol) and benzylacetone (3.83 g, 25.8 mmol) in ethanol (22 ml) was heated under reflux for 4 h. After cooling to room temperature, the mixture was filtered, and the residue washed with ethanol and dried under vacuum (0.25 mbar) to give 2.94 g (79%) of a white solid as one major isomer together with small amounts of other isomers. UV/Vis (ethanol): 268 (9400), 235 (11700), 218 (sh, 11800), 208 (14800), 204 (sh, 14000).

$^1$H-NMR (CDCl$_3$, major isomer): 8.95 (s, 2H); 7.35-7.24 (m, 4H); 7.24-7.15 (m, 6H); 2.92-2.82 (m, 4H); 2.71-2.61 (m, 4H); 2.60-2.49 (m, 4H); 1.82 (s, 6H); 1.75-1.66 (m, 4H).

$^{13}$C-NMR (CDCl$_3$, major isomer): 175.91 (s); 150.84 (s); 141.25 (d); 128.37 (d); 128.31 (d); 125.98 (d); 40.40 (t); 32.45 (t); 32.07 (t); 23.72 (t); 15.56 (q).

Preparation of 2-hydroxy-N',N',N',-tris[(1E,2E)-3-phenyl-2-propenylidene]-1,2,3-propanetricarbohydrazide (18c)

A mixture of 18a (0.80 g, 3.4 mmol) and trans cinnamic aldehyde (2.00 g, 15.3 mmol) in ethanol (50 ml) was heated under reflux for 3 h. After cooling to room temperature, the mixture was filtered, and the residue dried under vacuum to give 1.77 g (91%) of a pale yellow solid as a mixture of three isomers with respect to the amide bond conformation (E/Z/Z:E/Z/E:Z/Z/Z ca. 2:1:1).

UV/Vis (ethanol): 331 (sh, 21300), 315 (31600), 301 (sh, 27400), 240 (sh, 4700), 232 (7300), 224 (sh, 6000).

$^1$H-NMR: 11.44, 11.41, 11.35, 11.34, 11.16 (5 s, 3H); 8.30-8.24 (m, 1H); 8.00-7.94 (m, 1H); 7.86-7.80 (m, 1H); 7.66-7.50 (m, 6H); 7.43-7.25 (m, 9H); 7.10-6.84 (m, 6H); 6.10, 5.99, 5.95 (3s, 1H); 3.29-3.14 (m, 2H); 2.87-2.67 (m, 2H).

$^{13}$C-NMR: 171.52, 171.49, 170.35, 170.19, 169.94, 165.84, 165.76 (7 s); 149.70, 149.45, 149.24, 148.58, 148.48, 145.84, 145.67 (7 d); 139.06, 138.98, 138.57, 138.46, 138.40, 138.22 (6 d); 135.82, 135.78 (2 s); 128.73, 128.68 (2 d); 126.96, 126.91 (2 d); 125.69, 125.34, 125.31, 125.12 (4 d); 74.99, 74.76, 74.59 (3 s); 42.59, 42.29, 39.79, 39.49 (4 t).

Use of Active Aldehydes or Ketones

The following examples illustrate the formation of dynamic mixtures using perfuming or flavoring ingredients as active aldehydes or ketones. However, they are also representative for the generation of dynamic mixtures according to the present invention in which the active aldehydes or ketones are useful as insect repellants or attractants, or as bactericides or fungicides. Some of the compounds described in the following examples, such as benzaldehyde, decanal, 2,4-dimethyl-3-cyclohexene-1-carbaldehyde, 3,7-dimethyl-6-octenal(citronellal), 2-furancarbaldehyde(furfural), 4-hydroxy-3-methoxybenzaldehyde(vanillin), menthone, 1-(4-methylphenyl)-1-ethanone(4-methylacetophenone), 3-octanone, 2-pentyl-1-cyclopentanone(Delphone), 3-phenyl-2-propenal(cinnamic aldehyde), or 10-undecenal, are also known to be insect attractants or repellents (see for example: A. M. El-Sayed, The Pherobase 2005, http://www.pherobase.net) and/or to be active against bacteria (see for example: WO 01/24769 or EP 1 043 968).

Example 1

Formation of a Dynamic Mixture Using Girard-T Reagent as Hydrazine Derivative and Cinnamic Aldehyde as Perfuming Compound The formation the dynamic mixture was monitored by NMR spectroscopy in buffered aqueous solution ($D_2O$/$CD_3OD$ 2:1 (v/v)). An acidic deuterated buffer stock solution was prepared from the following product quantities:

| | |
|---|---|
| Ortho-phosphoric acid (origin: Fluka) | 0.0412 g |
| $KH_2PO_4$ (monobasic, origin: Acros) | 0.0290 g |
| Deuterium oxide | 1.5572 g |
| $CD_3OD$ | 0.6280 g |

Formation by Hydrolysis of the Hydrazone 3c

The formation of the invention's dynamic mixture by contacting hydrazone 3c and water was monitored by adding 0.7 ml of the deuterated buffer solution to 9.6 mg of 3e. $^1$H-NMR spectra were recorded at different time intervals on a Bruker AV 500 spectrometer using sodium 3-trimethylsilyltetradeuteriopropionate (DSP) as lock signal. The appearance of a doublet at 9.58 ppm indicated the formation of cinnamic aldehyde, the structure of which was confirmed by recording a $^{13}$C-NMR spectrum at the end of the experiment.

Formation by Reacting the Hydrazine Derivative 3a with Cinnamic Aldehyde

Similarly, formation of the invention's dynamic mixture by contacting 0.7 ml of the deuterated buffer solution and a mixture of 4.5 mg of cinnamic aldehyde and 5.9 mg of hydrazine derivative 3a was monitored by NMR. This resulted in the appearance of two doublets at 8.07 and 7.84 ppm, corresponding to the N=CH protons of the two isomers of hydrazone 3c. The identity of compound 3c was confirmed by $^{13}$C-NMR analysis of the reaction mixture at the equilibrium.

In both cases and under the given conditions the equilibrium is reached very rapidly (about 10-15 min).

Example 2

Measurement of Kinetic Rate Constants for the Formation of Dynamic Mixtures

The formation of the dynamic mixtures was monitored by UV/Vis spectroscopy and the kinetic rate constants were measured in buffered aqueous solution (water/ethanol 2:1 (v/v)) at a product concentration of ca. $1.7 \times 10^{-5}$ M.

a) Preparation of a Citric Acid Buffer Stock Solution Used as the Reaction Medium The following product quantities were weighed into a volumetric flask:

| | |
|---|---|
| NaOH (anhydrous pellets, origin: Carlo Erba) | 0.65 g |
| NaCl (origin: Carlo Erba) | 0.62 g |
| Citric acid (anhydrous, origin: Fluka) | 2.58 g |
| Demineralized water (MilliQ) | 160.02 g |
| Ethanol (absolute, origin: Carlo Erba) | 31.45 g |

10 ml of the buffer stock solution were diluted with 2 ml of ethanol to give a mixture of water/ethanol 2:1 (v/v) (corresponding to the final reaction solution used for the kinetic measurements). The pH value of this solution was 4.48 (±0.021), at 25.0° C. (±0.30).

b) Preparation of a Phosphoric Acid Buffer Stock Solution Used as the Reaction Medium The following product quantities were weighed into a volumetric flask:

| | |
|---|---|
| Ortho-phosphoric acid (origin: Fluka) | 1.97 g |
| $KH_2PO_4$ (monobasic, origin: Acros) | 1.37 g |
| NaCl (origin: Carlo Erba) | 0.60 g |
| Demineralized water (MilliQ) | 160.01 g |
| Ethanol (absolute, origin: Carlo Erba) | 31.45 g |

The pH value of the buffer in water/ethanol 2:1 (v/v) (obtained by diluting 10 ml of the buffer stock solution with 2 ml of ethanol) was 2.47 (±0.045), at 25.0° C. (±0.36).

c) Determination of the Equilibria of Dynamic Mixtures

All reactions were carried out in quartz cuvettes (1 cm) by adding either 0.2 ml of hydrazine derivative and 0.2 ml of cinnamic aldehyde (CA) or benzaldehyde (BA) (all at $2.0 \times 10^{-4}$ M in ethanol) to 2 ml of the buffer stock solution prepared above or, alternatively, by adding 0.4 ml of the corresponding hydrazone (at $1.0 \times 10^{-4}$ M in ethanol) to 2 ml of the buffer stock solution. UV/Vis spectra were recorded at constant time intervals between 240 and 450 nm. The first spectrum was recorded 2-3 min after addition of the compounds to the buffer solution, the following spectra were taken at intervals of 5 or 10 min (pH 2.47) or 30 or 60 min (pH 4.48), respectively.

If complete hydrolysis of the hydrazone takes place, the UV absorption at a given wavelength should change from that of the pure hydrazone ($A_h$) to reach the one corresponding to the mixture of the hydrazine derivative and the aldehyde/ketone ($A_{a+h}$). The inverse is expected for the formation of the hydrazone from the corresponding aldehyde/ketone and a hydrazine derivative. If in the course of the reaction the absorption approaches a constant value lying between these two extrema, an equilibrium state is reached and an "equilibrium value" $x_{eq}$ can be defined, which indicates to which point the reaction proceeds in either direction at a given wavelength ($\lambda$).

$$x_{eq}^f(\lambda) = \frac{A_{eq}^f - A_{a+h}}{A_h - A_{a+h}}$$

$$x_{eq}^h(\lambda) = 1 - \frac{A_h - A_{eq}^h}{A_h - A_{a+h}}$$

For a given dynamic mixture $x_{eq}^f$ is the equilibrium value for the formation of the dynamic mixture by contacting a hydrazine derivative with the aldehyde or ketone in water, $x_{eq}^h$ the equilibrium value for the dynamic mixture by contacting the hydrazone derivative with water, and $A_{eq}$ is the absorption reached at the equilibrium.

Under the conditions described above, the formation of a dynamic mixture either by hydrolysis of the hydrazone (1c, 2c, 2b or 14b) or by reaction between the hydrazine derivative (1a, 2a or 14a) and benzaldehyde or cinnamic aldehyde, respectively, gave the following equilibrium values $x_{eq}$ at λ=290 nm (BA) or λ=320 nm (CA):

| Equilibrium formation via reaction between the hydrazine derivative and the aldehyde | | | Equilibrium formation via hydrolysis of the hydrazone | | |
|---|---|---|---|---|---|
| hydrazine + aldehyde | $x_{eq}^f$ pH = 2.47 | $x_{eq}^f$ pH = 4.48 | hydrazone | $x_{eq}^h$ pH = 2.47 | $x_{eq}^h$ pH = 4.48 |
| 1a + BA | 0.09 | | 1b | 0.13 | |
| 1a + CA | 0.28 | 0.50 | 1c | 0.33 | 0.52 |
| 2a + BA | 0.19 | | 2b | 0.21 | |
| 2a + CA | 0.42 | 0.64 | 2c | 0.44 | 0.63 |
| 14a + BA | 0.18 | | 14b | 0.20 | |

If the values for $x_{eq}$ are both either 1 or 0, the hydrazone formation or the hydrazone hydrolysis go to completion, respectively. As can be noticed, the mixtures are the result of reversible reactions between various starting components, as the measured "equilibrium values" $x_{eq}$ are larger than 0 and smaller than 1.

Within the experimental error of the measurements, of approximately ±0.1, the same equilibrium state is reached independently of the stating point (i.e. hydrazine derivative, aldehyde and water or hydrazone and water).

It may happen, for other active aldehydes/ketones or hydrazine derivatives, that the equilibration is relatively slow, and that within the timeframe of the experiment such equilibrium is not fully reached, but this does not imply that the dynamic mixtures obtained by either contacting the hydrazine derivative and the active compound in water or by contacting the hydrazone derivative and water are not the same.

The UV/Vis spectra recorded for the formation and hydrolysis of hydrazone derivative 1c are shown in Figure (I).

d) Determination of the Rate Constants for the Formation of Various Dynamic Mixtures by Contacting the Hydrazine Derivatives and the Active Aldehydes/Ketones in Water Using the same reaction conditions as described above, see Example 2c), the rate constants were determined, from the change of absorption measured at 290 nm (benzaldehyde) or 320 nm (cinnamic aldehyde and vanillin), according to the method described by Guggenheim (Phil. Mag. [7] 1926, 2, 538-543). With Δt=1 or 2 h (pH 2.47) or Δt=7.5 or 15 h (pH 4.48), the kinetics were found to be of pseudo first order ($r^2$>0.99) and the following rate constants were obtained for the formation of hydrazine addition products:

| Hydrazine derivative | Active aldehyde or ketone | Rate constant in phosphoric acid buffer at pH = 2.47 $k_0$ [s$^{-1}$] | Rate constant in citric acid buffer at pH = 4.48 $k_0$ [s$^{-1}$] |
|---|---|---|---|
| 1a | benzaldehyde | 9.9 × 10$^{-4}$ | 4.2 × 10$^{-5}$ |
|  | cinnamic aldehyde | 3.3 × 10$^{-4}$ | 3.3 × 10$^{-5}$ |
|  | vanillin | 8.4 × 10$^{-4a}$) | |
| 2a | benzaldehyde | 6.1 × 10$^{-4}$ | 3.0 × 10$^{-5}$ |
|  | cinnamic aldehyde | 2.6 × 10$^{-4}$ | 2.6 × 10$^{-5}$ |
|  | vanillin | 6.4 × 10$^{-4}$ | |
| 3a | cinnamic aldehyde | 2.7 × 10$^{-4}$ | 1.7 × 10$^{-5}$ |
| 4a | benzaldehyde | 5.5 × 10$^{-4}$ | 1.6 × 10$^{-5}$ |
|  | cinnamic aldehyde | | 1.3 × 10$^{-5b}$) |
| 5a | benzaldehyde | 2.7 × 10$^{-4}$ | |
|  | cinnamic aldehyde | | 1.9 × 10$^{-5}$ |
| 6a | benzaldehyde | 1.3 × 10$^{-4}$ | |
|  | cinnamic aldehyde | 6.9 × 10$^{-5}$ | |
| 7a | cinnamic aldehyde | 9.8 × 10$^{-5}$ | 1.2 × 10$^{-5a}$) |
| 8a | benzaldehyde | 7.6 × 10$^{-5c}$) | |
|  | cinnamic aldehyde | 4.8 × 10$^{-5d}$) | 1.2 × 10$^{-5e}$) |
| 9a | cinnamic aldehyde | 2.3 × 10$^{-5f}$) | |
| 10a | benzaldehyde | 2.2 × 10$^{-4c}$) | |
| 11a | cinnamic aldehyde | 1.8 × 10$^{-4}$ | |
| 12a | vanillin | 9.0 × 10$^{-4g}$) | |
| 13a | benzaldehyde | 1.2 × 10$^{-3}$ | 5.1 × 10$^{-5}$ |
| 14a | benzaldehyde | 1.0 × 10$^{-3}$ | 6.8 × 10$^{-5}$ |
|  | cinnamic aldehyde | 3.5 × 10$^{-4}$ | |
|  | vanillin | 1.0 × 10$^{-3}$ | |
| 16a | cinnamic aldehyde | | 3.1 × 10$^{-5}$ |
| 17a | benzaldehyde | 1.0 × 10$^{-4a}$) | 3.0 × 10$^{-5c}$) |

$^a$)$r^2$ > 0.98;
$^b$)$r^2$ > 0.97;
$^c$)$r^2$ > 0.89;
$^d$)$r^2$ > 0.97, Δt = 5 h;
$^e$)$r^2$ ca. 0.97, Δt = 14 h;
$^f$)$r^2$ > 0.98, detection at 370 nm;
$^g$)$r^2$ > 0.96.

e) Determination of the Rate Constants for the Formation of Dynamic Mixtures by Contacting Hydrazone Derivatives and Water The UV/Vis spectra were recorded and the rate constants determined as described above to give the following values for the hydrolysis of hydrazones:

| Hydrazone | Active aldehyde or ketone | Rate constant in phosphoric acid buffer at pH = 2.47 $k_0$ [s$^{-1}$] | Rate constant in citric acid buffer at pH = 4.48 $k_0$ [s$^{-1}$] |
|---|---|---|---|
| 1b | benzaldehyde | 1.1 × 10$^{-3}$ | 3.0 × 10$^{-5}$ |
| 1c | cinnamic aldehyde | 3.3 × 10$^{-4}$ | 1.5 × 10$^{-5}$ |
| 2b | benzaldehyde | 6.4 × 10$^{-4}$ | 1.8 × 10$^{-5}$ |
| 2c | cinnamic aldehyde | 2.1 × 10$^{-4}$ | 8.5 × 10$^{-6}$ |
| 2d | vanillin | 6.6 × 10$^{-4}$ | |
| 3c | cinnamic aldehyde | 2.3 × 10$^{-4}$ | 6.9 × 10$^{-6}$ |
| 4b | benzaldehyde | 5.0 × 10$^{-4}$ | 9.0 × 10$^{-6}$ |
| 4c | cinnamic aldehyde | | 6.3 × 10$^{-6}$ |
| 5b | benzaldehyde | 2.2 × 10$^{-4}$ | |
| 5c | cinnamic aldehyde | | 5.7 × 10$^{-6}$ |
| 6b | benzaldehyde | 7.5 × 10$^{-5}$ | |
| 6c | cinnamic aldehyde | 1.7 × 10$^{-5a}$) | |
| 8b | benzaldehyde | 3.6 × 10$^{-5b}$) | |
| 8d | acetophenone | 1.5 × 10$^{-4c}$) | 1.0 × 10$^{-5c}$) |
| 14b | benzaldehyde | 1.1 × 10$^{-3}$ | 4.3 × 10$^{-5}$ |
| 14d | vanillin | 9.8 × 10$^{-4}$ | |
| 15b | benzaldehyde | 6.4 × 10$^{-4}$ | |
| 18c | cinnamic aldehyde | | 1.8 × 10$^{-5}$ |

$^a$) $r^2$ ca. 0.97, Δt = 5 h;
$^b$) $r^2$ > 0.98, Δt = 3.8 h, detection at 270 nm;
$^c$) detection at 270 nm.

Example 3

Performance of a Softener Base Comprising an Invention's Dynamic Mixture

The use as perfuming ingredient of the present invention's mixtures has been tested in a fabric softener.

A fabric softener base with the following composition has been prepared:

|  | Parts by weight |
|---|---|
| STEPANTEX ® VS90 or VHR90 (origin: Stepan) | 16.7 |
| STEPANQUAT ® F (origin: Stepan) | 0.4 |
| Dye (1% Sandolan Milling Blue N-LN 180; origin Clariant) | 0.3 |
| Water | 82.6 |
|  | 100.0 |

The perfuming performance, over time, of the free perfuming aldehydes/ketones and of the invention's mixtures (i.e. the free perfuming aldehydes/ketones with an hydrazine derivative as additive) was determined in the following experiments:

a) Fragrance Release from a Dynamic Mixture Containing Hydrazine Derivative 3a 1.80 g of the above fabric softener base were weighed into four small vials, respectively. Then 1 ml of a solution containing equimolar amounts (0.41 mmol) of 3-phenylbutanal (TRIFERNAL®, 60.7 mg), 10-undecenal (69.0 mg), (Z)-4-dodecenal (74.7 mg), (R)-3,7-dimethyl-6-octenal(citronellal, 63.3 mg), 4-phenyl-2-butanone(benzylacetone, 60.6 mg) and 1-phenyl-1-ethanone(acetophenone, 48.9 mg) in 10 ml of ethanol was added to each vial. Then, 1 ml of a solution containing 415.0 mg (2.48 mmol) of hydrazine derivative 3a in 10 ml of water was added to two of the samples, and 1 ml of water was added to the other two samples serving as the reference. All four samples were closed and left standing at room temperature to equilibrate. After 5 days, the samples were dispersed in a beaker with 600 ml of demineralized cold tap water, respectively. One cotton towel (EMPA cotton test cloth Nr. 221, origin: Eidgenössische Materialprüfanstalt (EMPA), pre-washed with an unperfumed detergent powder and cut to ca. 12×12 cm sheets) was added to each beaker and agitated manually for 3 min, left standing for 2 min, then wrung out by hand and weighed to obtain a constant quantity of residual water. Two of the towels (one with hydrazine derivative and one without) were analyzed immediately after treatment with the softener, the other two were left drying overnight and analyzed the next day. Each towel was put into an headspace sampling cell (160 ml) thermostatted at 25° C. and exposed to a constant air flow of 200 ml/min, respectively. The air was filtered through active charcoal and aspirated through a saturated solution of NaCl (to ensure a constant humidity of the air of ca. 75%). During 15 min the headspace system was left equilibrating, then the volatiles were adsorbed during 5 min (wet towels) or 15 min (dry towels) on a clean TENAX® cartridge, respectively. The sampling was repeated 7 times every 50 min (wet towels) or every hour (dry towels). The cartridges were desorbed on a Perkin Elmer TurboMatrix ATD desorber coupled to a Carlo Erba MFC 500 gas chromatograph equipped with a J&W Scientific DB1 capillary column (30 m, i.d. 0.45 mm, film 0.42 μm) and a FID detector. The volatiles were analyzed using a two step temperature gradient starting from 70° C. to 130° C. at 3° C./min and then going to 260° C. at 25° C./min. The injection temperature was at 240° C., the detector temperature at 260° C. Headspace concentrations (in ng/l) were obtained by external standard calibrations of the corresponding fragrance aldehydes and ketones using ethanol solutions of five different concentrations. 0.2 μl of each calibration solution was injected onto TENAX® cartridges, which were immediately desorbed under the same conditions as those resulting from the headspace sampling.

The following amounts of aldehydes and ketones were detected from the sample containing hydrazine derivative 3a as compared to the reference sample without 3a (in brackets):

|  | Wet 120 min [ng/l] | Wet 320 min [ng/l] | Dry 150 min [ng/l] | Dry 390 min [ng/l] |
|---|---|---|---|---|
| TRIFERNAL ® | 662.4 (663.4) | 427.1 (54.8) | 24.8 (3.5) | 29.6 (4.0) |
| 10-Undecenal | 2238.0 (2792.6) | 925.8 (109.6) | 37.8 (8.2) | 52.0 (11.6) |
| (Z)-4-Dodecenal | 1612.1 (2817.0) | 742.6 (762.8) | 27.0 (18.1) | 42.2 (30.3) |
| Citronellal | 1708.4 (68.5) | 310.9 (0) | 14.3 (2.2) | 14.1 (1.5) |
| Benzylacetone | 1212.2 (736.0) | 299.7 (130.7) | 5.2 (0.9) | 6.8 (1.2) |
| Acetophenone | 314.0 (318.9) | 72.5 (5.8) | 35.1 (1.8) | 43.1 (2.2) |

The data clearly illustrate that the presence of the hydrazine derivative 3a has a positive effect on the long-lastingness of the fragrance aldehydes and ketones. Especially the headspace concentrations measured at the end of the experiment on dry fabric were found to be between 1.4 ((Z)-4-dodecenal) and 20 (acetophenone) times higher in the presence of 3a than in its absence.

The kinetics of the fragrance release measured on dry fabric are illustrated in Figure (II).

b) Fragrance Release from a Dynamic Mixture Containing Hydrazine Derivative 14a

The experiment was carried out as described above by adding 1 ml of a solution containing equimolar amounts (0.81 mmol) of 2-furancarbaldehyde(furfural, 78.2 mg), 3-octanone (105.3 mg), 2,4,6-trimethyl-3-cyclohexene-1-carbaldehyde (125.5 mg), 1-(4-methylphenyl)-1-ethanone(4-methylacetophenone, 110.5 mg), 2-pentyl-1-cyclopentanone (Delphone, 126.2 mg) and (±)-exo-tricyclo[5.2.1.0(2,6)]decane-8exo-carbaldehyde (VERTRAL®, 135.2 mg) in 20 ml of ethanol to four vials each containing 1.80 g of the above fabric softener base. Then, 1 ml of a solution containing 214.4 mg (1.23 mmol) of hydrazine derivative 14a in 10 ml of water was added to two of the samples, and 1 ml of water was added to the other two samples serving as the reference.

The following amounts of aldehydes and ketones were detected from the sample containing hydrazine derivative 14a as compared to the reference sample without 14a (in brackets):

|  | Wet 120 min [ng/l] | Wet 320 min [ng/l] | Dry 150 min [ng/l] | Dry 390 min [ng/l] |
| --- | --- | --- | --- | --- |
| Furfural | 2.9 (88.3) | 2.3 (10.5) | 1.5 (1.0) | 1.3 (1.0) |
| 3-Octanone | 35.6 (0) | 7.4 (0) | 3.6 (0.1) | 2.6 (0.1) |
| 2,4,6-Trimethyl-3-cyclohexene-1-carbaldehyde | 4.7 (0) | 3.3 (0) | 0.8 (0) | 0.9 (0) |
| 4-Methylacetophenone | 48.6 (117.0) | 9.0 (12.5) | 0.8 (0.1) | 1.3 (0) |
| Delphone | 110.2 (32.8) | 53.3 (0) | 10.6 (0) | 14.5 (0) |
| VERTRAL ® | 123.5 (149.0) | 61.2 (12.9) | 29.6 (1.0) | 32.1 (0.7) |

The data clearly illustrate that the presence of the hydrazine derivative 14a has a positive effect on the long-lastingness of the fragrance aldehydes and ketones. The headspace concentrations measured on wet fabric were for some ingredients higher, and for some a little lower, in the presence of 14a than in its absence. However, the headspace concentrations measured on dry fabric at the end of the experiment were generally higher in the presence of 14a than in its absence.

c) Fragrance Release from a Dynamic Mixture Containing Hydrazine Derivative 16a

The experiment was carried out as described above by adding 1 ml of a solution containing equimolar amounts (0.41 mmol) of (−)-menthone (63.8 mg), (±)-exo-tricyclo[5.2.1.0(2,6)]decane-8exo-carbaldehyde (VERTRAL®, 67.8 mg), 3,5,5-trimethylhexanal (58.0 mg), (+)-(S)-1(6),8-p-menthadien-2-one(carvone, 61.4 mg), 4-(2,6,6-trimethyl-2-cyclohexen-1-yl)-2-butanone (α-dihydroionone, 80.1 mg) and decanal (63.3 mg) in 10 ml of ethanol to four vials each containing 1.80 g of the above fabric softener base. Then, 1 ml of a solution containing 218.9 mg (1.23 mmol) of hydrazine derivative 16a in 10 ml of water was added to two of the samples, and 1 ml of water was added to the other two samples serving as the reference.

The following amounts of aldehydes and ketones were detected from the sample containing hydrazine derivative 16a as compared to the reference sample without 16a (in brackets):

|  | Wet 120 min [ng/l] | Wet 320 min [ng/l] | Dry 150 min [ng/l] | Dry 390 min [ng/l] |
| --- | --- | --- | --- | --- |
| (−)-Menthone | 11.9 (5.5) | 7.3 (0) | 4.5 (0.2) | 4.5 (0) |
| VERTRAL ® | 46.4 (247.2) | 38.0 (20.9) | 6.7 (0.3) | 9.5 (0.4) |
| 3,5,5-Trimethylhexanal | 231.5 (4.9) | 168.2 (0) | 6.2 (1.7) | 6.7 (1.3) |
| (+)-Carvone | 63.7 (137.3) | 12.2 (13.5) | 1.7 (0) | 3.0 (0) |
| α-Dihydroionone | 33.6 (122.0) | 26.9 (11.5) | 5.5 (1.1) | 6.9 (2.3) |
| Decanal | 12.8 (536.9) | 16.4 (20.4) | 3.6 (1.4) | 5.0 (1.4) |

The data clearly illustrate that the presence of the hydrazine derivative 16a has a positive effect on the long-lastingness of the fragrance aldehydes and ketones. The headspace concentrations measured on wet fabric were for some ingredients higher, and for some a little lower, in the presence of 16a than in its absence. However, the headspace concentrations measured on dry fabric at the end of the experiment were higher in the presence of 16a than in its absence.

d) Fragrance Release from a Dynamic Mixture Containing Hydrazine Derivative 18a

The experiment was carried out as described above by adding 1 ml of a solution containing equimolar amounts (0.41 mmol) of 2-furancarbaldehyde(furfural, 39.1 mg), 10-undecenal (69.0 mg), benzaldehyde (44.0 mg), (R)-3,7-dimethyl-6-octenal(citronellal, 63.4 mg), 2-pentyl-1-cyclopentanone (Delphone, 62.7 mg) and 1-(4-methylphenyl)-1-ethanone(4-methylacetophenone, 54.6 mg) in 10 ml of ethanol to four vials each containing 1.80 g of the above fabric softener base. Then, 1 ml of a solution containing 192.1 mg (0.82 mmol) of hydrazine derivative 18a in 10 ml of water was added to two of the samples, and 1 ml of water was added to the other two samples serving as the reference.

The following amounts of aldehydes and ketones were detected from the sample containing hydrazine derivative 18a as compared to the reference sample without 18a (in brackets):

|  | Wet 120 min [ng/l] | Wet 320 min [ng/l] | Dry 150 min [ng/l] | Dry 390 min [ng/l] |
| --- | --- | --- | --- | --- |
| Furfural | 95.2 (527.5) | 62.1 (18.1) | 21.7 (5.6) | 15.5 (3.3) |
| 10-Undecenal | 116.9 (1762.7) | 79.1 (268.1) | 13.4 (3.2) | 16.0 (3.5) |
| Benzaldehyde | 172.0 (14.3) | 97.7 (0) | 66.4 (9.4) | 54.2 (9.9) |
| Citronellal | 63.8 (67.3) | 46.2 (0) | 4.0 (0) | 3.9 (0) |
| Delphone | 286.7 (69.7) | 138.3 (0) | 75.3 (0) | 66.9 (0) |
| 4-Methylacetophenone | 427.2 (822.4) | 113.4 (0) | 55.0 (0) | 64.9 (0) |

The data clearly illustrate that the presence of the hydrazine derivative 18a has a positive effect on the long-lastingness of the fragrance aldehydes and ketones. As in the previous example, the positive effect was found for five of the fragrance molecules on wet and for all six compounds on dry fabric. The headspace concentrations measured on dry fabric at the end of the experiment were all between 4 (citronellal) and 60 (4-methylacetophenone) times higher in the presence of 18a than in its absence.

The same experiment was carried out with the humidity of the air being ca. 33% (by aspirating the air through a saturated solution of $MgCl_2$). The measured headspace concentrations on dry fabric were found to be in the same order of magnitude as those recorded at an air humidity of 75%.

e) Fragrance Release from a Dynamic Mixture Containing Hydrazine Derivative 19a

The experiment was carried out as described above by adding 1 ml of a solution containing equimolar amounts (0.41 mmol) of 5-methyl-3-heptanone (52.9 mg), 2,4-dimethyl-3-cyclohexene-1-carbaldehyde (TRIPLAL®, 56.3 mg), 4-ethylbenzaldehyde (55.1 mg), 6-methoxy-2,6-dimethylheptanal (methoxymelonal, 70.4 mg), (+)-(S)-1(6),8-p-menthadien-2-one (carvone, 61.5 mg) and 2-methyldecanal (69.8 mg) in 10 ml of ethanol to four vials each containing 1.80 g of the above fabric softener base. Then, 1 ml of a solution containing 211.5 mg (2.46 mmol) of hydrazine derivative 19a in 10 ml of water was added to two of the samples, and 1 ml of water was added to the other two samples serving as the reference.

The following amounts of aldehydes and ketones were detected from the sample containing hydrazine derivative 19a as compared to the reference sample without 19a (in brackets):

|  | Wet 120 min [ng/l] | Wet 320 min [ng/l] | Dry 150 min [ng/l] | Dry 390 min [ng/l] |
| --- | --- | --- | --- | --- |
| 5-Methyl-3-heptanone | 67.0 (0) | 35.3 (0) | 6.0 (3.4) | 4.0 (0.6) |
| TRIPLAL ® | 39.0 (6.3) | 26.2 (0) | 22.7 (16.8) | 14.8 (10.4) |
| 4-Ethylbenzaldehyde | 0 (17.5) | 1.2 (0) | 0.9 (0) | 0.9 (0) |
| Methoxymelonal | 21.4 (121.4) | 18.6 (61.6) | 5.6 (1.1) | 6.4 (1.5) |
| (+)-Carvone | 43.9 (96.2) | 5.9 (3.1) | 0.5 (0) | 0.5 (0) |
| 2-Methyldecanal | 21.6 (370.4) | 15.4 (11.0) | 8.8 (1.6) | 8.2 (1.1) |

The data clearly illustrate that the presence of the hydrazine derivative 19a has a positive effect on the long-lastingness of the fragrance aldehydes and ketones. The headspace concentrations measured on wet fabric were for some ingredients higher, and for some a little lower, in the presence of 19a than in its absence. However, the headspace concentrations measured on dry fabric at the end of the experiment were generally higher in the presence of 19a than in its absence.

f) Fragrance Release from a Dynamic Mixture Containing Hydrazone Derivatives 1d, 1e, 2e, 8d, 9b and 4e The experiment was carried out as described above by adding 1 ml of a solution containing hydrazone derivatives 1d (112.8 mg), 1e (118.0 mg), 2e (107.6 mg), 8d (117.8 mg), 9b (98.3 mg) and 14e (89.2 mg) in 10 ml of ethanol to two vials, respectively, each containing 1.80 g of the above fabric softener base. Then, 1 ml of a solution containing equimolar amounts (0.41 mmol) of (R)-3,7-dimethyl-6-octenal(citronellal, 63.3 mg), 3-phenylbutanal (TRIFERNAL®, 60.9 mg), 10-undecenal (69.5 mg), benzaldehyde (43.6 mg), 4-phenyl-2-butanone(benzylacetone, 60.9 mg) and 1-phenyl-1-ethanone(acetophenone, 48.7 mg) in 10 ml ethanol was added to another two vials, respectively, each containing 1.80 g of the above fabric softener base, and serving as the reference.

The following amounts of aldehydes and ketones were detected from the sample containing the mixture of hydrazone derivatives as compared to the reference sample with the corresponding fragrance molecules (in brackets):

|  | Wet 120 min [ng/l] | Wet 320 min [ng/l] | Dry 150 min [ng/l] | Dry 390 min [ng/l] |
|---|---|---|---|---|
| Citronellal | 212.6 (9.5) | 68.7 (0) | 14.3 (0.3) | 17.2 (0.1) |
| TRIFERNAL ® | 80.5 (173.4) | 44.3 (20.2) | 3.7 (1.6) | 5.5 (1.2) |
| 10-Undecenal | 88.4 (531.5) | 42.0 (56.9) | 5.6 (5.9) | 8.3 (4.5) |
| Benzaldehyde | 9.5 (5.7) | 15.5 (0) | 4.7 (0.1) | 5.4 (0.6) |
| Benzylacetone | 167.8 (161.5) | 66.0 (38.1) | 14.8 (0.7) | 15.9 (0.5) |
| Acetophenone | 42.9 (78.7) | 9.1 (2.4) | 5.6 (0.4) | 5.3 (0.3) |

The data clearly illustrate that the dynamic mixture obtained from the hydrazone derivatives has a positive effect on the long-lastingness of the fragrance aldehydes and ketones as compared to the unmodified free fragrance molecules.

The headspace concentrations measured on wet or dry fabric were for all ingredients, except one, higher in the sample containing the hydrazone derivatives than in the sample with the fragrances. The only exception was 10-undecenal, nevertheless a positive effect of the dynamic mixture was obtained on dry fabric.

Example 4

Washing Cycle Using a Softener Base Comprising an Invention's Dynamic Mixture

The use as perfuming ingredient of the present invention's dynamic mixtures in a softener base was tested by olfactive evaluation on fabric after a machine-washing cycle.

A fabric softener base with the following composition has been prepared:

|  | Parts by weight |
|---|---|
| STEPANTEX ® VK90 (origin: Stepan) | 16.5 |
| Calcium chloride | 0.2 |
| Water | 83.3 |
|  | 100.0 |

Fragrance accords containing active aldehydes and ketones together with other perfuming co-ingredients with the following composition were used:

| Accord 1: | |
|---|---|
|  | Parts by weight |
| Methyl benzoate | 15 |
| Coumarin | 60 |
| IRALIA TOTAL ® | 30 |
| 3,7-Dimethyl-1,6-octadien-3-ol (linalool) | 180 |
| 1-Methoxy-4-methylbenzene (methylparacresol) | 5 |
| HEDIONE ® | 290 |
| NIRVANOL ® (origin: Firmenich SA) | 20 |
| 2-Phenylethanol | 200 |
|  | 800 |

| Accord 2: | |
|---|---|
|  | Parts by weight |
| 10-Undecenal | 100 |
| Methyl benzoate | 15 |
| 4-Phenyl-2-butanone (benzylacetone) | 100 |
| Coumarin | 60 |
| IRALIA TOTAL ® | 30 |
| Linalool | 180 |
| Methylparacresol | 5 |
| HEDIONE ® | 290 |
| NIRVANOL ® | 20 |
| 2-Phenylethanol | 200 |
|  | 1000 |

Dynamic mixtures were prepared by adding either 100 mg of 10-undecenal or, alternatively, 1 g of either one of the above mentioned accords, respectively, to 100 g of the fabric softener base described above. Then 0.5 or 1.0 molar equivalent of hydrazine derivative 4a or 14a with respect to the total amount of active aldehyde or ketone in the mixture was added. The resulting mixtures were shaken for 5 min, and then left equilibrating for at least 5 d at room temperature prior to a use in a wash test.

For the olfactive evaluation, the following dynamic mixtures were prepared:

| Entry | Fragrance raw material or accord added to softener base | Hydrazine derivative added to softener base | Molar equivalent of hydrazine derivative with respect to the amount of active fragrance aldehyde or ketone |
|---|---|---|---|
| 1 | 10-Undecenal | 14a | 1.0 |
| 2 | 10-Undecenal | 14a | 0.5 |
| 3 | 10-Undecenal | 4a | 1.0 |
| 4 | 10-Undecenal | 4a | 0.5 |
| 5 | Accord 1 | 14a | 1.0 |
| 6 | Accord 2 | 14a | 1.0 |

For the wash test, three large cotton terry towels (45×90 cm) and three small cotton terry towels (28×28 cm) were washed in a Miele Novotronic W300-33CH washing machine with 85 g of an unperfumed detergent powder (Via, origin: Unilever, Stockholm, Sweden), using a short cycle at 40° C. with 900 RPM for the spinning cycle. Once the cycle was finished 2.5 l of water were added to the machine through the dispensing tray, and a new short cycle called "ammidonage" was started. As soon as the machine was drawing water, a solution of 35 g of the fabric softener bases (containing either one of the above mentioned dynamic mixtures) diluted into 2.5 l of water was added via the dispensing tray. Once the cycle was finished the cotton terry towels were line dried for 24 h and then evaluated by two experts.

All evaluations were done in comparison to a control sample that did not contain any hydrazine (or hydrazone) derivative. Accords were compared to the corresponding accord that did not contain the hydrazine derivative. The following results were obtained:

Entry 1: Just out of the washing machine the odor of 10-undecenal was much weaker in the presence of hydrazine derivative 14a when compared to a sample perfumed with just the aldehyde. However, after 3, 7 and 14 d, the sample containing the invention's dynamic mixture was clearly stronger than the control sample without the hydrazine derivative.

Entries 2, 3 and 4: The same effect as in Entry 1 was observed. The perception of the aldehydic note was prolonged in the presence of the dynamic mixture, whereas the control sample without hydrazine derivative did not smell anymore after 3 d of drying.

Entry 5: After 3, 7 and 14 d, the sample containing the dynamic mixture was found to have a clearly stronger and fresher odor with a better volume than the reference sample without hydrazine derivative 14a.

Entry 6: Again, the odor resulting from the sample containing the dynamic mixture was perceived as stronger and fresher and had more volume than the reference sample without hydrazine derivative 14a.

The samples containing the dynamic mixtures according to the invention were always rated stronger and fresher after 3, 7 and 14 d after the wash. The effect resulting from the presence of the hydrazine derivative is clearly perceived, and the presence of the invention's dynamic mixture thus helps to retain fresher notes on dry fabric.

Example 5

Performance of a Shampoo Base Comprising an Invention's Dynamic Mixture

The use as perfuming ingredient of the present invention's mixtures has been tested in a shampoo.

A shampoo base with the following composition has been prepared:

| | Parts by weight |
|---|---|
| TEXAPON ® NSO IS, sodium laureth sulfate (origin: Henkel) | 48.0 |
| DEHYTON ® AB-30, coco-betaine (origin: Henkel) | 7.0 |
| Dow Corning 2-1691 Emulsion (origin: Dow Corning) | 3.0 |
| Rewomid IPP 240, cocamide MIPA (origin: Witco Surfactants) | 1.2 |
| Cetyl alcohol | 1.2 |
| Cithrol EGDS 3432, ethylene glycol distearate (origin: Croda) | 0.7 |
| Jaguar Excel, guar hydroxypropyltrimmonium chloride (origin: Rhodia) | 0.4 |
| GLYDANT ® Plus Liquid, preservative (origin: Lonza) | 0.3 |
| Deionized water | 38.2 |
| | 100.0 |

The perfuming performance, over time, of the free perfuming aldehydes/ketones and of the invention's mixtures (i.e. the free perfuming aldehydes/ketones with an hydrazine derivative as additive) has been determined in the following experiments:

a) Fragrance Release from a Dynamic Mixture Containing Hydrazine Derivative 20a 2.00 g of the above shampoo base were weighed into four small vials, respectively. Then 200 μl of a solution containing equimolar amounts (0.6 mmol) of 3,5,5-trimethylhexanal (85.3 mg), (R)-3,7-dimethyl-6-octenal(citronellal, 92.6 mg), decanal (93.9 mg), 4-phenyl-2-butanone(benzylacetone, 89.0 mg), 10-undecenal (100.9 mg) and (±)-exo-tricyclo[5.2.1.0 (2,6)]decane-8exo-carbaldehyde (VERTRAL®, 98.8 mg) in 10 ml of ethanol were added to each vial. Furthermore, to two of the samples 13.7 mg (0.072 mmol) of hydrazine derivative 20a were added. The four samples were then closed and left standing at room temperature to equilibrate for 5 d. Four hair swatches (ca. 5 g, origin: A. & C. Sécher Fesnoux, Industrie du cheveu, Chaville, France) were wetted with tap water (at ca. 35° C.), washed with 1.0 g of the above mentioned unperfumed shampoo base and rinsed with water, respectively. Two of the hair swatches were then washed for 1 min with 0.5 g of the shampoo base containing the perfumery aldehydes and ketones together with hydrazine derivative 20a, the other two with 0.5 g of the shampoo base containing only the perfumery aldehydes and ketones. The hair swatches were each rinsed for 30 s. The washing was repeated a second time with another 0.5 g of the respective shampoo bases. After leaving for 2 min, the swatches were rinsed with water (at 25° C.) for 1 min and pre-dried shortly with household paper. Two of the swatches (one with hydrazine derivative 20a and one without) were analyzed immediately after treatment with the shampoo, the other two were left drying overnight and analyzed the next day. Each hair swatch was put into a headspace sampling cell (160 ml) thermostatted at 25° C. and exposed to a constant air flow of 200 ml/min, respectively. The air was filtered through active charcoal and aspirated through a saturated solution of NaCl (to ensure a constant humidity of the air of ca. 75%). During 55 min the headspace system was left equilibrating, then the volatiles were adsorbed during 10 min (wet swatches) or 15 min (dry swatches) on a clean Tenax® cartridge. The sampling was repeated 8 times every 30 min. The cartridges were desorbed on a Perkin Elmer ATD-400 desorber coupled to an Agilent 6890 N gas chromatograph equipped with an Agilent HP 5 HS capillary column (30 m, i.d. 0.25 mm, film 0.25 μm) and an Agilent MSD 5973 N mass sensitive detector. The volatiles were analyzed using a two-step temperature gradient starting from 70° C. to 130° C. at 3° C./min and then going to 260° C. at 25° C./min. The injection temperature was at 240° C., the detector temperature at 260° C., the inlet pressure at 62 kPa. Headspace concentrations (in ng/l) were obtained by external standard calibrations of the corresponding fragrance aldehydes and ketones using ethanol solutions of five different concentrations. 1 μl of each calibration solution was injected onto TENAX® cartridges, which were immediately desorbed under the same conditions as those resulting from the headspace sampling.

The following amounts of aldehydes and ketones were detected from the sample containing hydrazine derivative 20a as compared to the reference sample without 20a (in brackets):

|                      | Wet 225 min [ng/l] | Wet 385 min [ng/l] | Dry 255 min [ng/l] | Dry 435 min [ng/l] |
|---|---|---|---|---|
| 3,5,5-Trimethylhexanal | 378.7 (82.9)  | 182.7 (49.9)  | 11.6 (4.2)  | 23.6 (6.5)  |
| Citronellal          | 176.4 (113.8) | 121.0 (92.0)  | 9.4 (3.3)   | 8.7 (3.1)   |
| Decanal              | 187.1 (174.8) | 149.0 (139.3) | 25.3 (23.5) | 38.5 (21.1) |
| Benzylacetone        | 151.3 (114.0) | 135.5 (105.4) | 9.9 (9.5)   | 11.6 (10.9) |
| 10-Undecenal         | 76.4 (78.1)   | >63.0 (63.5)  | 11.3 (11.1) | 9.3 (10.5)  |
| VERTRAL ®            | 186.6 (82.8)  | 135.2 (65.6)  | 18.0 (5.6)  | 14.4 (5.4)  |

The data clearly illustrate that the presence of the hydrazine derivative 20a has a positive effect on the long-lastingness of the fragrance aldehydes and ketones. The headspace concentrations measured on wet and on dry hair are generally higher (or at least equal) in the presence of the hydrazine derivative than in its absence. Whereas in the case of 10-undecenal equal headspace concentrations were measured in both cases, the presence of the hydrazine derivative 20a increased the headspace concentration of 3,5,5-trimethylhexanal by a factor of 3 (dry hair) to 4 (wet hair) as compared to the reference sample without 20a. It is therefore possible to use a complex perfuming composition and modify the evaporation behavior of only a part of the ingredients while maintaining the others unchanged.

b) Fragrance Release from a Dynamic Mixture Containing Hydrazone Derivative 12d

The experiment was carried out as described above by adding 200 µl of a solution containing 3,5,5-trimethylhexanal (85.4 mg) in 10 ml of ethanol to two of the vials, and 3.4 mg (0.012 mmol) of hydrazone derivative 12d to the other two vials.

The following amounts of aldehyde was detected from the sample containing hydrazone derivative 12d as compared to the reference sample with the corresponding fragrance molecule (in brackets):

|                        | Wet 225 min [ng/l] | Wet 385 min [ng/l] | Dry 255 min [ng/l] | Dry 435 min [ng/l] |
|---|---|---|---|---|
| 3,5,5-Trimethylhexanal | 443.0 (55.1)       | 220.0 (33.2)       | 24.9 (3.6)         | 24.2 (3.0)         |

The data clearly illustrate that the dynamic mixture obtained from hydrazone derivative 12d has a positive effect on the long-lastingness of the fragrance aldehyde as compared to the unmodified free fragrance molecules.

What is claimed is:

1. A delivery system in the form of a dynamic mixture obtainable by reacting:
   i) at least one hydrazine derivative of formula

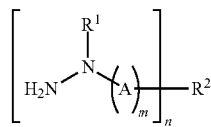

(I)

wherein
   $R^1$ represents a hydrogen atom, a $C_1$ to $C_5$ alkyl group or a phenyl group optionally substituted by up to three $R^3$ groups;
   $R^3$ represents a group selected from the group consisting of OR, $NR_2$, $SO_3R$, $C_{1-4}$ alkyl group and COOR, R representing a hydrogen atom, a $C_1$ to $C_{10}$ alkyl or polyethylene- or polypropylene-glycol group, a phenyl group or a $C_6$ to $C_9$ alkylaryl group;
   A represents a functional group selected from the group consisting of C=O, $SO_2$, C=S and C=NR;
   and m is 0 or 1; n is 1, 2, 3 or 4; and $R^2$ represents a mono-, di-, tri- or tetra-radical from a $C_1$ to $C_{18}$ linear, branched or cyclic hydrocarbon group optionally comprising one, two, or three nitrogen or oxygen atoms, or from a phenyl group, or from a $C_{4-5}$ hetero-aromatic group, the $R^2$ being optionally substituted by up to three $R^3$ groups;
   with
   ii) at least one volatile perfuming ingredient comprising an active aldehyde or ketone having a molecular weight of between 80 and 230 g/mol;
   with the reacting conducted in a water-containing medium to reversibly form a hydrazone derivative.

2. A delivery system according to claim 1, wherein the water-containing medium comprises at least 30% w/w of water.

3. A delivery system according to claim 1, wherein the hydrazine derivative is a compound of formula

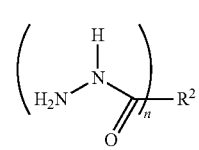

(II)

wherein
n is 1, 2, 3 or 4 and $R^2$ represents a mono-, di-, tri- or tetra-radical derived from a $C_1$ to $C_6$ linear, branched or cyclic hydrocarbon group optionally comprising up to two nitrogen or oxygen atoms, or from a phenyl group or from a $C_{4-5}$ hetero-aromatic group, the $R^2$ being optionally substituted by one or two $R^3$ groups;
$R^3$ representing a group selected from the group consisting of OR, $NR_2$, $SO_3R$, $C_{1-4}$ alkyl group and COOR, R representing a hydrogen atom, a $C_1$ to $C_5$ alkyl or polyethylene- or polypropylene-glycol group, a phenyl group or a $C_{6-7}$ alkylaryl group.

4. A delivery system according to claim 1, wherein the hydrazine derivative is:
$(NH_2NHCO)_n$-Alk, wherein n is comprised between 1 and 4 and Alk is a $C_2$-$C_{18}$ linear, branched or cyclic hydrocarbon group optionally substituted by two OH groups and optionally containing one or two nitrogen atoms.

5. A delivery system according to claim 1, wherein the volatile perfuming ingredient is an active aldehyde or ketone compound having a vapor pressure above 2.0 Pa.

6. A delivery system according to claim 1, wherein the volatile perfuming ingredient is an active aldehyde or ketone compound having a vapor pressure above 5.0 Pa.

7. A delivery system according to claim 1, wherein the volatile perfuming ingredient is an active aldehyde or ketone compound having that is selected from the group consisting of the $C_{6-20}$ perfuming aldehydes and the $C_{6-20}$ perfuming ketones.

8. A perfuming composition comprising:
   i) as perfuming ingredient, a delivery system as defined in claim 1;
   ii) at least one ingredient selected from the group consisting of a perfumery carrier and a perfumery base; and
   iii) optionally at least one perfumery adjuvant.

9. A consumer article comprising:
   i) as a perfuming component, a delivery system, as defined in claim 1; and
   ii) a liquid consumer product base.

10. A perfumed article according to claim 9, wherein the consumer product base is a liquid detergent or fabric softener, a perfume, cologne or after-shave lotion, a perfumed liquid soap, a shower or bath mousse, oil or gel, a hygiene product or a hair care product, a shampoos, a body-care product, a liquid based deodorant or antiperspirant, an air freshener comprising a liquid perfuming ingredient, a cosmetic preparation, a fabric refresher, an ironing water, a paper, a wipe or bleach.

11. A consumer article comprising:
   i) the delivery system according to claim 1; and
   ii) a solid consumer product base intended to be used in presence of water.

12. A method to confer, enhance, improve or modify the odor properties of a perfuming composition or of a perfumed article, which method comprises adding to the composition or article an effective amount of the delivery system as defined in of claim 1.

13. A method to prolong the perfuming effect of a perfuming composition containing at least one perfuming and water, the method comprising forming the perfuming composition of claim 8 in order to prolong the perfuming effect of the perfuming ingredient during application or use of the perfuming composition.

14. A delivery system according to claim 4, wherein Alk is $C_1$, $C_2$, $C_3$, $C_4$, $C_5$, $C_6$, $C_8$, $C_{12}$, $C_{16}$, $C_{18}$, $(CHOH)_2$, or $CH_2(CHOH)_2CH_2$.

15. A delivery system according to claim 1, wherein the volatile perfuming ingredient is a perfuming, flavoring, insect repellent or attractant, bactericide or fungicide ingredient.

16. A delivery system in the form of a dynamic mixture obtained by reacting:
   i) at least one hydrazine derivative of formula

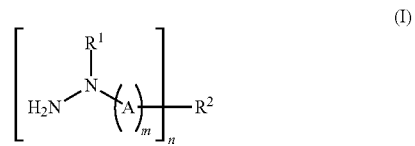

wherein
   $R^4$ represents a hydrogen atom, a $C_1$ to $C_5$ alkyl group or a phenyl group optionally substituted by up to three $R^3$ groups;
   $R^3$ represents a group selected from the group consisting of OR, $NR_2$, $SO_3R$, $C_{1-4}$ alkyl group and COOR, R representing a hydrogen atom, a $C_1$ to $C_{10}$ alkyl or polyethylene- or polypropylene-glycol group, a phenyl group or a $C_6$ to $C_9$ alkylaryl group;
   A represents a functional group selected from the group consisting of C=O, $SO_2$, C=S and C=NR; and
   m is 0 or 1; n is 1, 2, 3 or 4; and $R^2$ represents a mono-, di-, tri- or tetra-radical derived from a $C_1$ to $C_{18}$ linear, branched or cyclic hydrocarbon group optionally comprising one, two, or three nitrogen or oxygen atoms, or derived from a phenyl group, or derived from a $C_{4-5}$ hetero-aromatic group, the $R^2$ being optionally substituted by up to three $R^3$ groups; with
   ii) at least one volatile perfuming ingredient containing an active aldehyde or ketone having a molecular weight of between 80 and 230 g/mol and having a vapor pressure above 2.0 Pa.,
   with the reacting conducted in a water-containing medium to reversibly form a hydrazone derivative.

17. A delivery system according to claim 1, wherein n is 1 and $R^2$ represents a $CH_2NMe_3X$ or a $CH_2$—$(NC_5H_4)X$ group, X representing a halogen atom.

* * * * *

UNITED STATES PATENT AND TRADEMARK OFFICE
CERTIFICATE OF CORRECTION

PATENT NO. : 8,124,578 B2  Page 1 of 1
APPLICATION NO. : 11/669560
DATED : February 28, 2012
INVENTOR(S) : Lehn et al.

It is certified that error appears in the above-identified patent and that said Letters Patent is hereby corrected as shown below:

Column 40:
Line 22 (claim 16, second line after formula (I)), change "$R^4$" to -- $R^1$ --.

Signed and Sealed this
Eighth Day of January, 2013

David J. Kappos
*Director of the United States Patent and Trademark Office*